(12) United States Patent
Ono et al.

(10) Patent No.: US 8,415,490 B2
(45) Date of Patent: Apr. 9, 2013

(54) EPOXY COMPOUND AND MANUFACTURING METHOD THEREOF

(75) Inventors: Koutaro Ono, Moriyama (JP); Michiya Ishikawa, Moriyama (JP); Jiro Nakatani, Moriyama (JP)

(73) Assignee: Toray Fine Chemicals Co., Ltd. (JP)

( * ) Notice: Subject to any disclaimer, the term of this patent is extended or adjusted under 35 U.S.C. 154(b) by 0 days.

(21) Appl. No.: 12/989,482

(22) PCT Filed: Oct. 13, 2009

(86) PCT No.: PCT/JP2009/067694
§ 371 (c)(1),
(2), (4) Date: Oct. 25, 2010

(87) PCT Pub. No.: WO2010/047244
PCT Pub. Date: Apr. 29, 2010

(65) Prior Publication Data
US 2011/0040111 A1 Feb. 17, 2011

(30) Foreign Application Priority Data

Oct. 20, 2008 (JP) .................................. 2008-269732
Mar. 11, 2009 (JP) .................................. 2009-058151

(51) Int. Cl.
*C07D 303/36* (2006.01)
*C07D 301/27* (2006.01)

(52) U.S. Cl. ........................................ 549/552; 549/514

(58) Field of Classification Search .................. 549/514, 549/551, 552
See application file for complete search history.

(56) References Cited

U.S. PATENT DOCUMENTS 4,487,948 A 12/1984 Shimp et al.
4,814,414 A 3/1989 Newman-Evans

FOREIGN PATENT DOCUMENTS

| EP | 2 412 742 A1 | 2/2012 |
|---|---|---|
| JP | 59-196314 A | 11/1984 |
| JP | 1-1235374 A | 5/1989 |
| JP | 7-292315 A | 11/1995 |
| JP | 2003-113223 A | 4/2003 |
| JP | 2003-119244 A | 4/2003 |
| JP | 2004-263153 A | 9/2004 |
| JP | 2006-152135 A | 6/2006 |

OTHER PUBLICATIONS

Mi, X. et al., "Synthesis and Characterization of a Novel Epoxy Resin Derived from Amino-Terminated (aryl ether ketone)," *American Chemical Society, Division of Polymer Chemistry*, 2003, vol. 44, No. 2, p. 8.

*Primary Examiner* — Taylor Victor Oh
(74) *Attorney, Agent, or Firm* — DLA Piper LLP (US)

(57) ABSTRACT

A novel epoxy compound represented by the following formula and a method for producing the same are provided:

[Chem. 1]

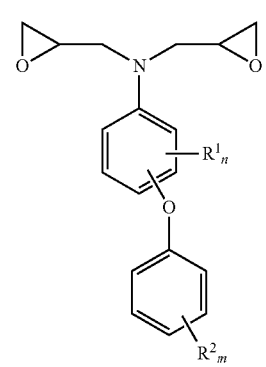

wherein $R^1$ and $R^2$ are members selected from the group consisting of hydrogen, aliphatic hydrocarbon group having 1 to 4 carbon atoms, alicyclic hydrocarbon group having 3 to 6 carbon atoms, aromatic hydrocarbon group having 6 to 10 carbon atoms, halogen atom, ether group, ester group, acyl group and nitro group, n is an integer of 1 to 4, and m is an integer of 1 to 5.

16 Claims, 18 Drawing Sheets

EPOXY COMPOUND AND MANUFACTURING METHOD THEREOF

RELATED APPLICATIONS

This is a §371 of International Application No. PCT/JP2009/067694, with an international filing date of Oct. 13, 2009 (WO 2010/047244 A1, published Apr. 29, 2010), which is based on Japanese Patent Application Nos. 2008-269732, filed Oct. 20, 2008, and 2009-058151, filed Mar. 11, 2009, the subject matter of which is incorporated by reference.

TECHNICAL FIELD

This disclosure relates to a novel epoxy compound useful in the industry and a method for producing the same.

BACKGROUND

Epoxy compounds are compounds that have been used in the organic chemistry field and the polymer chemistry field and are compounds that are useful in a wide variety of fields for industrial applications, such as fine chemicals, medical and agrochemical intermediates, raw materials of resins, and further electronic information materials and optical materials.

Moreover, multifunctional epoxy compounds are cured with various curing agents to become cured products that are commonly excellent in mechanical properties, water resistance, chemical resistance, heat resistance and electric properties and, therefore, they have been used in a wide variety of fields, such as adhesive, paint, laminated boards, and composite materials.

Conventionally N,N-diglycidylaniline and N,N-diglycidylanilines having an alkyl group having 1 to 4 carbon atoms have been known as epoxy compounds having an N,N-diglycidylaniline skeleton. However, when N,N-diglycidylaniline and the N,N-diglycidylanilines having an alkyl group of 1 to 4 carbon atoms was cured with an amine, the cured epoxy resin with sufficient strength was not obtained (see JP 2003-113223 A and JP 2003-119244 A).

Thus, improvements in cured epoxy resins in performance, such as strength, elastic modulus, adhesiveness, toughness, heat resistance, weather resistance, solvent resistance, and impact resistance, has been desired in various fields. It could therefore be helpful to provide an epoxy compound that improves the performance of a cured epoxy resin, and a method for the production thereof.

SUMMARY

We thus provide an epoxy compound from which a high-performance cured epoxy resin can be obtained and a method for producing the same.

That is, our epoxy compound is an epoxy compound represented by the following formula:

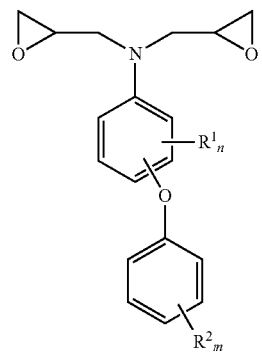

[Chem. 1]

wherein $R^1$ and $R^2$ are members selected from the group consisting of hydrogen, aliphatic hydrocarbon group having 1 to 4 carbon atoms, alicyclic hydrocarbon group having 3 to 6 carbon atoms, aromatic hydrocarbon group having 6 to 10 carbon atoms, halogen atom, ether group, ester group, acyl group and nitro group, n is an integer of 1 to 4, and m is an integer of 1 to 5.

The method for producing an epoxy compound is a method for producing an epoxy compound represented by the following formula:

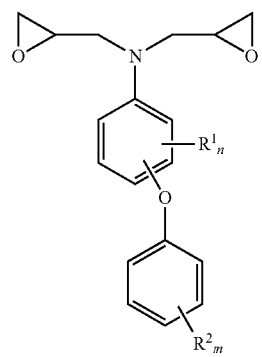

[Chem. 3]

wherein $R^1$ and $R^2$ are members selected from the group consisting of hydrogen, aliphatic hydrocarbon group having 1 to 4 carbon atoms, alicyclic hydrocarbon group having 3 to 6 carbon atoms, aromatic hydrocarbon group having 6 to 10 carbon atoms, halogen atom, ether group, ester group, acyl group and nitro group, n is an integer of 1 to 4, and m is an integer of 1 to 5, comprising the step of reacting a phenoxyaniline derivative represented by the following formula:

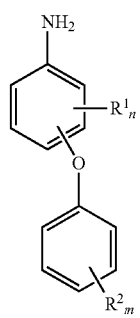

[Chem. 2]

wherein $R^1$ and $R^2$ are members selected from the group consisting of hydrogen, aliphatic hydrocarbon group having 1 to 4 carbon atoms, alicyclic hydrocarbon group having 3 to 6 carbon atoms, aromatic hydrocarbon group having 6 to 10 carbon atoms, halogen atom, ether group, ester group, acyl group and nitro group, n is an integer of 1 to 4, and m is an integer of 1 to 5 and epichlorohydrin.

By curing the epoxy compound with a curing agent, a high-performance cured epoxy resin that is high in strength, elastic modulus, adhesiveness, toughness, heat resistance, weather resistance, solvent resistance, impact resistance, and so on can be obtained. Moreover, by mixing the epoxy compound and an ordinary epoxy resin and curing them with an amine, a cured product that can be used for adhesive or paint, for example, can be obtained.

The epoxy compound is useful in a wide variety of fields for industrial applications, such as fine chemicals, medical and agrochemical intermediates, raw materials of resins, and further electronic information materials and optical materials.

The method for producing an epoxy compound can produce a useful epoxy compound in good yield.

DETAILED DESCRIPTION

Figure 1:
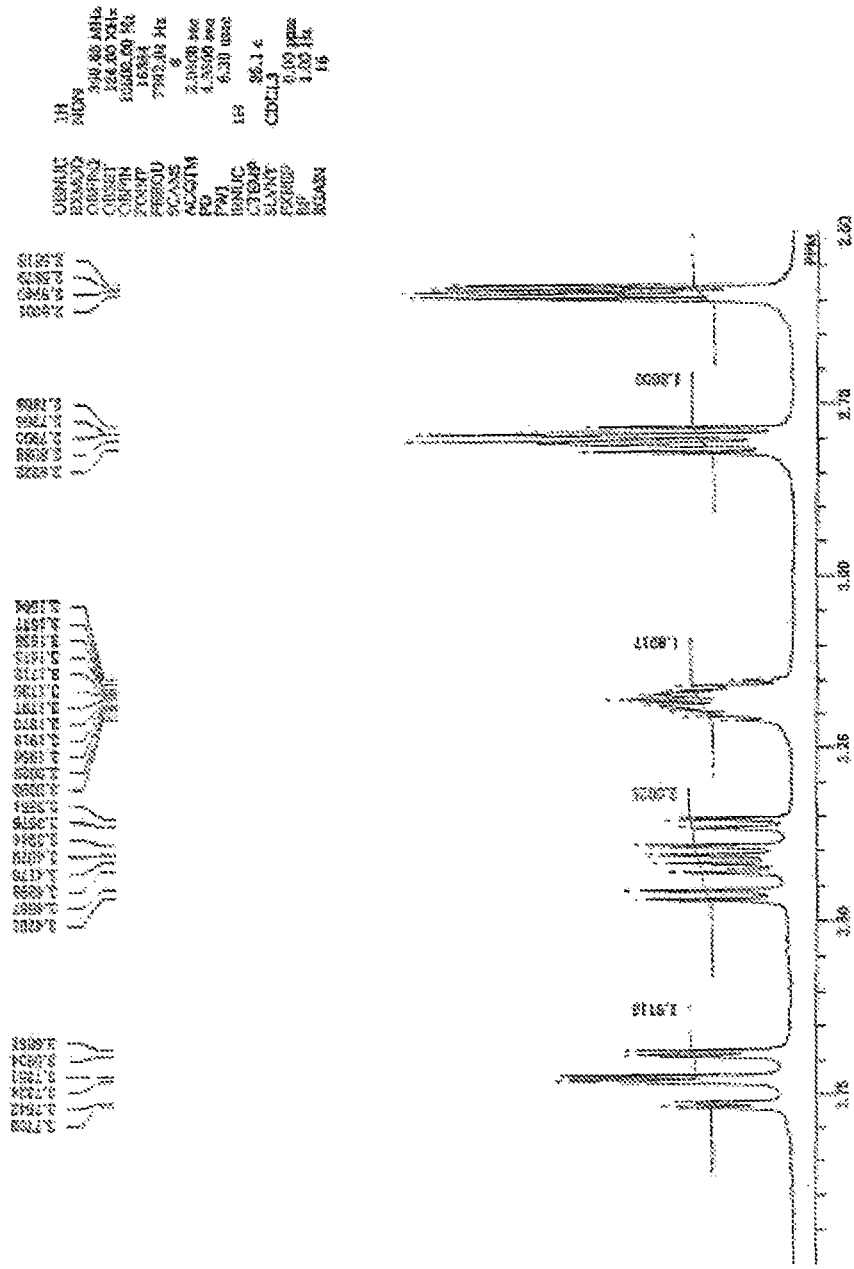
FIG. 1 is a partial enlarged diagram of the $^1$H-NMR chart of the 4-phenoxy-N,N-diglycidylaniline obtained in Example 2.

The epoxy compound and a method for the production thereof are described in detail below.

The epoxy compound is an epoxy compound represented by the following formula:

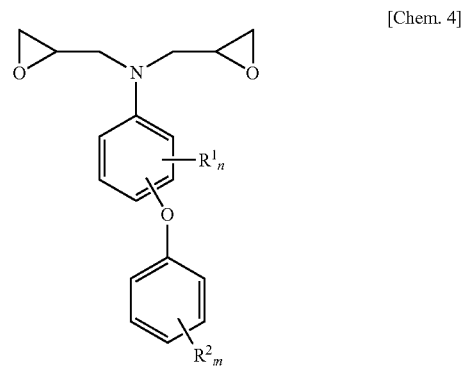

[Chem. 4]

wherein $R^1$ and $R^2$ are members selected from the group consisting of hydrogen, aliphatic hydrocarbon group having 1 to 4 carbon atoms, alicyclic hydrocarbon group having 3 to 6 carbon atoms, aromatic hydrocarbon group having 6 to 10 carbon atoms, halogen atom, ether group, ester group, acyl group and nitro group, n is an integer of 1 to 4, and m is an integer of 1 to 5.

In the epoxy compound, $R^1$ is preferably hydrogen, an aliphatic hydrocarbon group having 1 to 4 carbon atoms, or an aromatic hydrocarbon group having 6 to 9 carbon atoms, and $R^1$ is more preferably hydrogen.

In the epoxy compound, $R^2$ is preferably hydrogen, an aliphatic hydrocarbon group having 1 to 4 carbon atoms, or a nitro group, and $R^2$ is more preferably hydrogen, a methyl group, or a nitro group.

The epoxy compound is even more preferably an epoxy compound represented by the following formula:

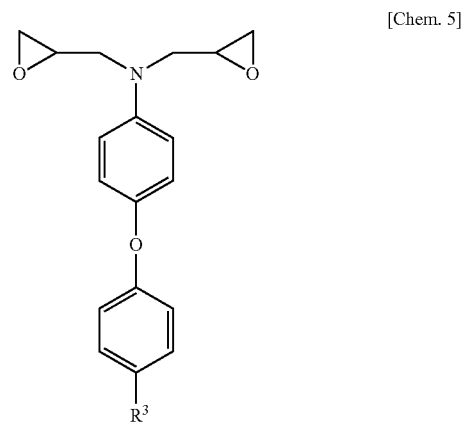

[Chem. 5]

wherein $R^3$ is hydrogen, a methyl group, or a nitro group, an epoxy compound represented by the following formula:

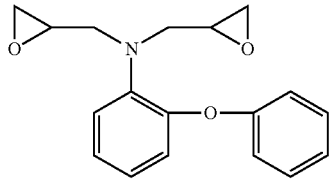
[Chem. 6]

or an epoxy compound represented by the following formula:

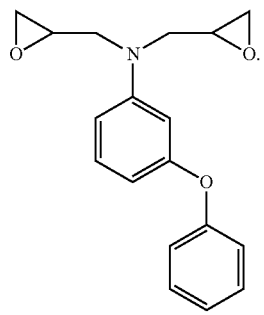
[Chem. 7]

The epoxy compound can be cured with a curing agent for ordinary epoxy resins. A high-performance cured epoxy resin that is high in strength, elastic modulus, adhesiveness, toughness, heat resistance, weather resistance, solvent resistance, impact resistance, and so on can be obtained by curing the epoxy compound with an amine. The epoxy compound becomes a cured product with a moderate elastic modulus when it is cured with metaxylenediamine, for example.

The method for producing an epoxy compound is a method of producing an epoxy compound represented by the following formula:

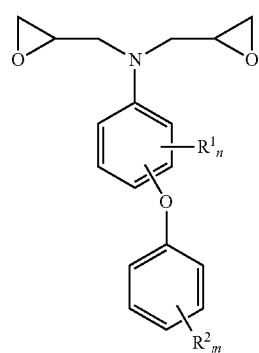
[Chem. 9]

wherein $R^1$ and $R^2$ are members selected from the group consisting of hydrogen, aliphatic hydrocarbon group having 1 to 4 carbon atoms, alicyclic hydrocarbon group having 3 to 6 carbon atoms, aromatic hydrocarbon group having 6 to 10 carbon atoms, halogen atom, ether group, ester group, acyl group and nitro group, n is an integer of 1 to 4, and m is an integer of 1 to 5, comprising the step of reacting a phenoxyaniline derivative represented by the following formula:

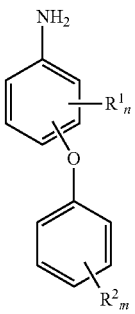
[Chem. 8]

wherein $R^1$ and $R^2$ are members selected from the group consisting of hydrogen, aliphatic hydrocarbon group having 1 to 4 carbon atoms, alicyclic hydrocarbon group having 3 to 6 carbon atoms, aromatic hydrocarbon group having 6 to 10 carbon atoms, halogen atom, ether group, ester group, acyl group and nitro group, n is an integer of 1 to 4, and m is an integer of 1 to 5, and epichlorohydrin.

In the method for producing an epoxy compound, $R^1$ is preferably hydrogen, an aliphatic hydrocarbon group having 1 to 4 carbon atoms, or an aromatic hydrocarbon group having 6 to 9 carbon atoms, and $R^1$ is more preferably hydrogen.

In the method for producing an epoxy compound, $R^2$ is preferably hydrogen or an aliphatic hydrocarbon group having 1 to 4 carbon atoms or a nitro group, and $R^2$ is more preferably hydrogen, a methyl group, or a nitro group.

Specific examples of the phenoxyaniline derivative in the method for producing an epoxy compound include 4-phenoxyaniline, 3-phenoxyaniline, 2-phenoxyaniline, 4-(4-methylphenoxy)aniline, 4-(3-methylphenoxy)aniline, 4-(2-methylphenoxy)aniline, 3-(4-methylphenoxy)aniline, 3-(3-methylphenoxy)aniline, 3-(2-methylphenoxy)aniline, 2-(4-methylphenoxy)aniline, 2-(3-methylphenoxy)aniline, 2-(2-methylphenoxy)aniline, 4-(4-ethylphenoxy)aniline, 4-(3-ethylphenoxy)aniline, 4-(2-ethylphenoxy)aniline, 4-(4-propylphenoxy)aniline, 4-(4-tert-butylphenoxy)aniline, 4-(4-cyclohexylphenoxy)aniline, 4-(3-cyclohexylphenoxy)aniline, 4-(2-cyclohexylphenoxy)aniline, 4-(4-naphthylphenoxy)aniline, 4-(3-naphthylphenoxy)aniline, 4-(4-methoxyphenoxy)aniline, 4-(3-methoxyphenoxy)aniline, 4-(2-methoxyphenoxy)aniline, 2,4-bis(2-methylphenoxy)aniline, 4-(3-phenoxyphenoxy)aniline, 4-(4-phenoxyphenoxy)aniline, 4-[4-(trifluoromethyl)phenoxy]aniline, 4-[3-(trifluoromethyl)phenoxy]aniline, 4-[2-(trifluoromethyl)phenoxy]aniline, 4-(2-naphthyloxy)aniline, 4-(1-naphthyloxy)aniline, 4-[(1,1'-biphenyl-4-yl)oxy]aniline, dibenzofuran-2-amine, 8-amino-1-nitrodibenzofuran, 3-methoxy-2-dibenzofuranamine, 4-(4-nitrophenoxy)aniline, 4-(3-nitrophenoxy)aniline, 4-(2-nitrophenoxy)aniline, 3-nitro-4-aminophenyl phenyl ether, 2-nitro-4-(4-nitrophenoxy)aniline, 4-(2,4-dinitrophenoxy)aniline, 3-nitro-4-phenoxyaniline, 4-(2-chlorophenoxy)aniline, 4-(3-chlorophenoxy)aniline, 4-(4-chlorophenoxy)aniline, 4-(2,4-dichlorophenoxy)aniline, 3-chloro-4-(4-chlorophenoxy)aniline, 4-(4-chloro-m-tolyloxy)aniline, and 3-chloro-4-(4-aminophenoxy)methyl benzoate. Particularly, 4-phenoxyaniline, 3-phenoxyaniline, 2-phenoxyaniline, 4-(4-methylphenoxy)aniline, 2-(2-methylphenoxy)aniline, 4-(4-nitrophenoxy)aniline, 4-(2-naphthyloxy)aniline, and 4-(1-naphthyloxy)aniline are used preferably.

In the method for producing an epoxy compound, the amount of the epichlorohydrin used is preferably 2 mol to 20 mol, and more preferably 4 mol to 10 mol per mol of the phenoxyaniline derivative. If the amount of the epichlorohydrin used is less than 2 mol, a large amount of a residual monochlorohydrin derivative may remain and, as a result, the yield of the desired dichlorohydrin derivative may become low. If the amount of the epichlorohydrin used exceeds 20 mol, a large amount of energy may be needed for separating a desired product from a reaction solution containing unreacted epichlorohydrin after the reaction and the amount of waste may become larger, so that economical disadvantage may increase.

The reaction temperature is preferably 40 to 150° C., and more preferably 50 to 120° C.

As to the method of feeding raw materials in the method for producing an epoxy compound, epichlorohydrin or a solution of epichlorohydrin may be added to a phenoxyaniline derivative or a solution containing a phenoxyaniline derivative. Alternatively, a phenoxyaniline derivative or a solution containing a phenoxyaniline derivative may be added to epichlorohydrin or a solution containing epichlorohydrin.

In the method for producing an epoxy compound, it is desirable to control the rate of adding raw materials according to the rate of reaction to prevent rapid generation of heat and runaway of reaction. The time during which the raw materials are added is preferably 0.5 to 6 hours.

The reaction time is usually 0.5 to 60 hours under stirring after the end of the addition of the raw materials.

The time at which the amount of remaining monochlorohydrin contained in the reaction solution becomes minimum is considered as an indicator of the end of the reaction.

The method for producing an epoxy compound can be carried out either in the absence of a solvent or in the presence of a solvent. In the method for producing an epoxy compound, it is preferable to react a phenoxyaniline derivative with epichlorohydrin in a solvent containing an alcohol.

Specific examples of the alcohol to be used preferably in the method for producing an epoxy compound include primary alcohols, such as methanol, ethanol, 1-propanol, 1-butanol, 1-pentanol, and 1-hexanol, secondary alcohols, such as isopropanol, 2-butanol, 2-pentanol, 3-pentanol, 2-hexanol, cyclohexanol, 2-heptanol, and 3-heptanol, tert-butanol, tert-pentanol, ethylene glycol, ethylene glycol monomethyl ether, ethylene glycol monoethyl ether, ethylene glycol mono-n-propyl ether, ethylene glycol mono-n-dibutyl ether, ethylene glycol monophenyl ether, diethylene glycol, diethylene glycol monomethyl ether, diethylene glycol monoethyl ether, diethylene glycol mono-n-propyl ether, diethylene glycol mono-n-butyl ether, triethylene glycol, triethylene glycol monomethyl ether, triethylene glycol mono-n-butyl ether, propylene glycol, propylene glycol monomethyl ether, propylene glycol monoethyl ether, propylene glycol mono-n-propyl ether, propylene glycol mono-n-butyl ether, propylene glycol monophenyl ether, dipropylene glycol, dipropylene glycol monomethyl ether, dipropylene glycol monoethyl ether, dipropylene glycol mono-n-propyl ether, dipropylene glycol mono-n-butyl ether, tripropylene glycol, tripropylene glycol monomethyl ether, and tripropylene glycol mono-n-butyl ether. Especially, methanol, ethanol, 1-propanol, and isopropanol are used particularly preferably.

The used amount of the solvent containing an alcohol is preferably 2 to 20 times by weight, and more preferably 2 to 10 times by weight that of the phenoxyaniline derivative.

In the method for producing an epoxy compound, a phenoxyaniline derivative and epichlorohydrin are preferably react in a solvent containing an alcohol, and then the formed dichlorohydrin derivative represented by the following formula:

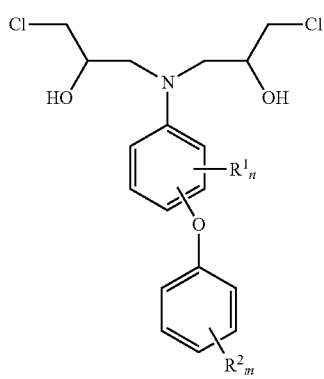

[Chem. 10]

wherein $R^1$ and $R^2$ are members selected from the group consisting of hydrogen, aliphatic hydrocarbon group having 1 to 4 carbon atoms, alicyclic hydrocarbon group having 3 to 6 carbon atoms, aromatic hydrocarbon group having 6 to 10 carbon atoms, halogen atom, ether group, ester group, acyl group and nitro group, n is an integer of 1 to 4, and m is an integer of 1 to 5, react with an alkali compound, and producing a diepoxy compound by dehydrochlorination.

In the method for producing an epoxy compound, examples of an alkali compound that is preferably used include lithium hydroxide, sodium hydroxide, potassium hydroxide, barium hydroxide, magnesium hydroxide, calcium hydroxide, lithium carbonate, sodium carbonate, potassium carbonate, barium carbonate, magnesium carbonate, calcium carbonate, lithium hydrogencarbonate, sodium hydrogencarbonate, potassium hydrogencarbonate, lithium hydride, sodium hydride, potassium hydride, sodium methoxide, potassium methoxide, sodium ethoxide, potassium ethoxide, sodium n-propoxide, potassium n-propoxide, sodium isopropoxide, potassium isopropoxide, sodium n-butoxide, potassium n-butoxide, sodium tert-butoxide, potassium tert-butoxide, sodium tert-amylate, potassium tert-amylate, sodium n-hexylate, potassium n-hexylate, and tetramethylammonium hydroxide. Especially, sodium hydroxide and potassium hydroxide are used preferably.

An alkali compound may be put as it is, it also may be added dropwise in the form of an aqueous solution or an alcoholic solution.

The alkali compound is used in a molar amount of 1 to 10 times the molar amount of the dichlorohydrin derivative.

In the method for producing an epoxy compound, it is desirable to make a quaternary ammonium salt and/or a quaternary phosphonium salt coexist in converting a dichlorohydrin derivative into a diepoxy compound. By adding a quaternary ammonium salt and/or a quaternary phosphonium salt and making them coexist, a reaction is accelerated and the yield of the epoxy compound increases.

Preferred examples of a quaternary ammonium salt to be used include bromides, chlorides, iodides, hydrogensulfates, hydroxides, and so on of tetramethylammonium, trimethylethylammonium, dimethyldiethylammonium, triethyl-methylammonium, tripropyl-methylammonium, tributyl-methylammonium, trioctyl-methylammonium, tetraethylammonium, trimethylpropylammonium, trimethylphenylammonium, benzyltrimethylammonium, benzyltriethylammonium, diallyldimethylammonium, n-octyltrimethylammonium, stearyltrimethylammonium, cetyldimethylethylammonium, tetrapropylammonium, tetran-butylammonium, beta-methylcholine, tetra-n-butylammonium, phenyltrimethylammonium, and the like.

Bromides, chlorides, hydrogensulfates, and hydroxides of trioctyl-methylammonium, tetraethylammonium, benzyltrimethylammonium, benzyltriethylammonium, and tetra-n-butylammonium are particularly preferred.

Preferred examples of a quaternary phosphonium salt to be used include bromides, chlorides, iodides, hydrogensulfates, hydroxides, and so on of tetramethylphosphonium, trimethylethylphosphonium, dimethyldiethylphosphonium, triethylmethylphosphonium, tripropylmethylphosphonium, tributylmethylphosphonium, trioctyl-methylphosphonium, tetraethylphosphonium, trimethyl-propylphosphonium, trimethylphenylphosphonium, benzyltrimethylphosphonium, diallyldimethylphosphonium, n-octyltrimethylphosphonium, stearyltrimethylphosphonium, cetyldimethylethylphosphonium, tetrapropylphosphonium, tetra-n-butylphosphonium, tetra-n-butylphosphonium, phenyltrimethylphosphonium, methyltriphenylphosphonium, ethyltriphenyl phosphonium, tetraphenylphosphonium, and the like.

The amount of the quaternary ammonium salt and/or the quaternary phosphonium salt added may be a catalytic amount, and it is preferably 0.001 to 0.5 times by mol the amount of the phenoxyaniline derivative.

The method for producing an epoxy compound may be either in a one-step process in which an addition step and a cyclization step are advanced in a system simultaneously or in a two-step process in which a cyclization step is advanced after the completion of an addition step.

The method for producing an epoxy compound is preferably carried out in the two-step process in which a cyclization step is advanced after the completion of an addition step because an epoxy compound of a high purity is obtained.

When the method for producing an epoxy compound is carried out in a two-step process in which a cyclization step is advanced after the completion of an addition step, the reaction temperature of the cyclization step is preferably 0 to 90° C., and more preferably 30 to 80° C. The reaction time is preferably 0.5 to 10 hours after the end of the addition of the alkali compound.

When the method for producing an epoxy compound is carried out in a two-step process in which a cyclization step is advanced after the completion of an addition step, an alcohol solvent, a hydrocarbon solvent, an ether solvent, and an ester solvent are preferably used as a solvent for the cyclization step.

Especially, methanol, ethanol, 1-propanol, 1-butanol, isopropanol, 2-butanol, and tert-butanol are preferable as an alcohol solvent.

Examples of the hydrocarbon solvent include hexane, 2-methylpentane, 2,2-dimethylbutane, 2,3-dimethylbutane, heptane, octane, isooctane, nonane, trimethyl hexane, decane, dodecane, benzene, toluene, xylene, ethylbenzene, cumene, mesitylene, cyclohexyl-benzene, diethylbenzene, cyclopentane, methylcyclopentane, cyclohexane, methylcyclohexane, and ethylcyclohexane.

Examples of the ether solvent include diisopropyl ether, dibutyl ether, dihexyl ether, anisole, phenetole, diphenyl ether, tetrahydrofuran, tetrahydropyran, ethylene glycol dibutyl ether, diethylene glycol dimethyl ether, diethylene glycol diethyl ether, and diethylene glycol dibutyl ether.

Examples of the ester solvent include methyl acetate, ethyl acetate, propyl acetate, isopropyl acetate, butyl acetate, and isobutyl acetate.

Hydrocarbon solvents that are preferably used are cyclohexane, toluene, xylene, ethylbenzene, cumene, mesitylene, and diethylbenzene.

In the method for producing an epoxy compound, isolation of the desired product, i.e., the epoxy compound, can be achieved preferably by a combination of common unit operations, such as (1) evaporation of a reaction solvent, (2) extraction with a hydrophobic solvent, (3) evaporation of an extraction solvent, (4) distillation, and (5) crystallization.

For example, an organic solvent such as toluene is added to a liquid resulting from a cyclization reaction and a desired product is extracted to the oil layer. Then the aqueous layer is separated and removed. Moreover, it is preferable to completely remove inorganic salts dissolved in the obtained oil layer by washing the oil layer with water. The amount of the organic solvent used is preferably 0.2 to 50 times by weight, and more preferably 1 to 20 times by weight that of the desired product.

The desired product can be obtained by evaporating the solvent out of the obtained oil layer with heating under reduced pressure. By distilling this product, it is also possible to obtain a product with a higher purity. The distillation is preferably carried out under reduced pressure and, specifically, it is preferably carried out at a pressure reduction of 0.1 to 700 Pa and a distillation temperature of 200 to 350° C.

Moreover, it is easy to increase the purity by isolating an epoxy compound, which is the desired product, from the obtained oil layer by crystallization. Examples of the method of crystallization include cooling crystallization, concentrating crystallization, and poor solvent crystallization.

EXAMPLES

Our compounds and methods are described concretely below with reference to examples.

Example 1

To a four-necked flask equipped with a thermometer, a dropping funnel, a cooling tube, and a stirrer was charged with 610.6 g (6.6 mol) of epichlorohydrin, and then the inside of the four-necked flask was purged with nitrogen. In 1018.5 g of ethanol was dissolved 203.7 g (1.1 mol) of 4-phenoxyaniline powder. The temperature of the epichlorohydrin was raised to 70° C. and the ethanolic solution of 4-phenoxyaniline was dropped over 4 hours. Moreover, the reaction was continued at 70° C. for six hours under stirring to produce 4-phenoxy-N,N-bis(2-hydroxy-3-chloropropyl)aniline.

Subsequently, the temperature in the flask was lowered to 30° C. or lower and then 229.2 g (2.75 mol) of a 48% aqueous NaOH solution was dropped over two hours. Moreover, a reaction was made advance for one hour under stirring, so that a cyclization reaction was carried out.

The completion of the cyclization reaction was confirmed by liquid chromatography and then ethanol was removed by distillation. To the resulting concentrate was added 407.4 g of toluene, followed by extraction. Then washing with 407.4 g of 5% brine was repeated twice. The removal of toluene and epichlorohydrin from the organic layer under reduced pressure provided 308.5 g (purity: 91.3% (GC area %)) of a brown viscous liquid containing 4-phenoxy-N,N-diglycidylaniline as a main component. The yield of 4-phenoxy-N,N-diglycidylaniline calculated as a pure compound (on the basis of 4-phenoxyaniline) was 86.1%.

Example 2

The brown viscous liquid obtained in Example 1 was subjected to simple distillation at a pressure of 100 Pa and a temperature of 250° C., yielding 4-phenoxy-N,N-diglycidylaniline with a purity of 96.1% (GC area %) (yellow viscous liquid).

Figure 2:
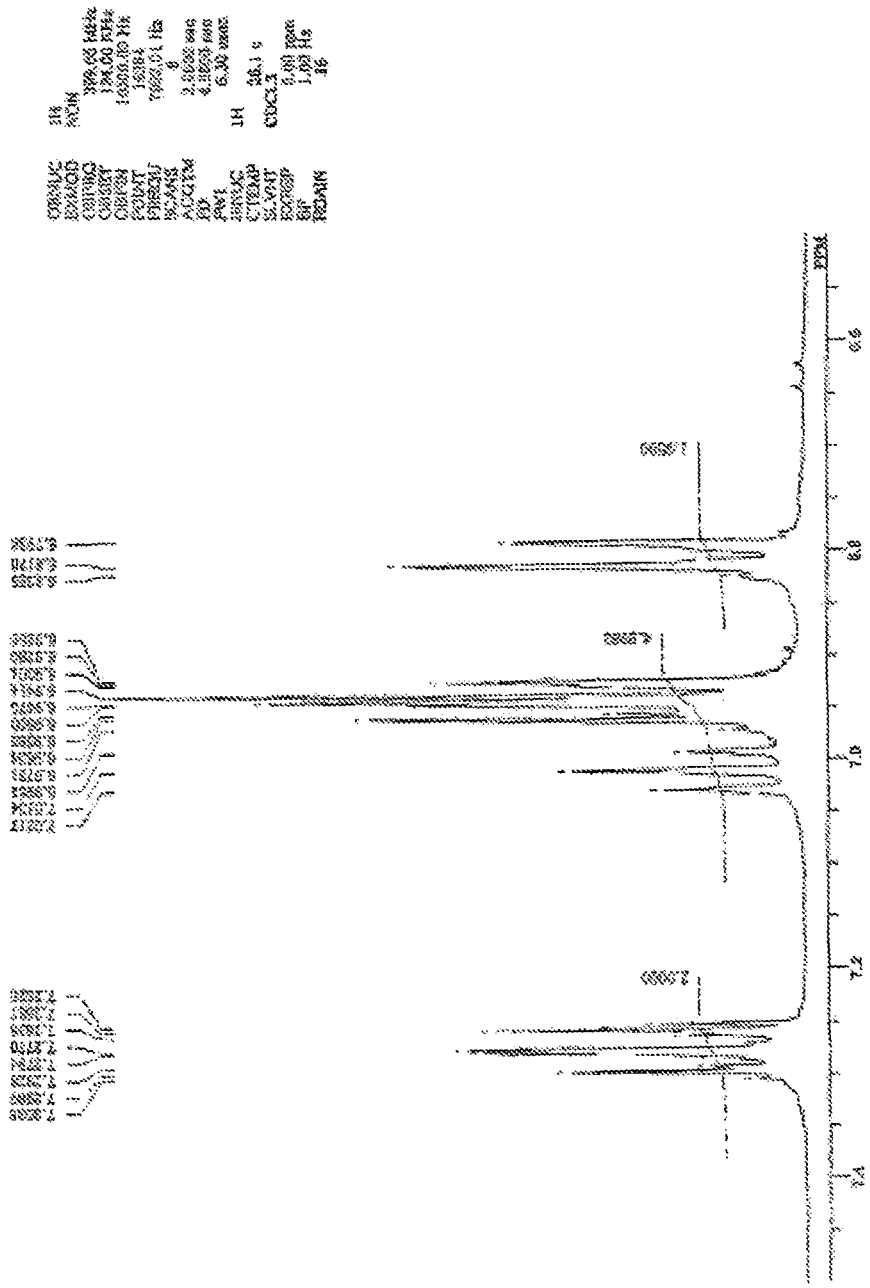
FIG. 2 is a partial enlarged diagram of the $^1$H-NMR chart of the 4-phenoxy-N,N-diglycidylaniline obtained in Example 2.
Figure 3:
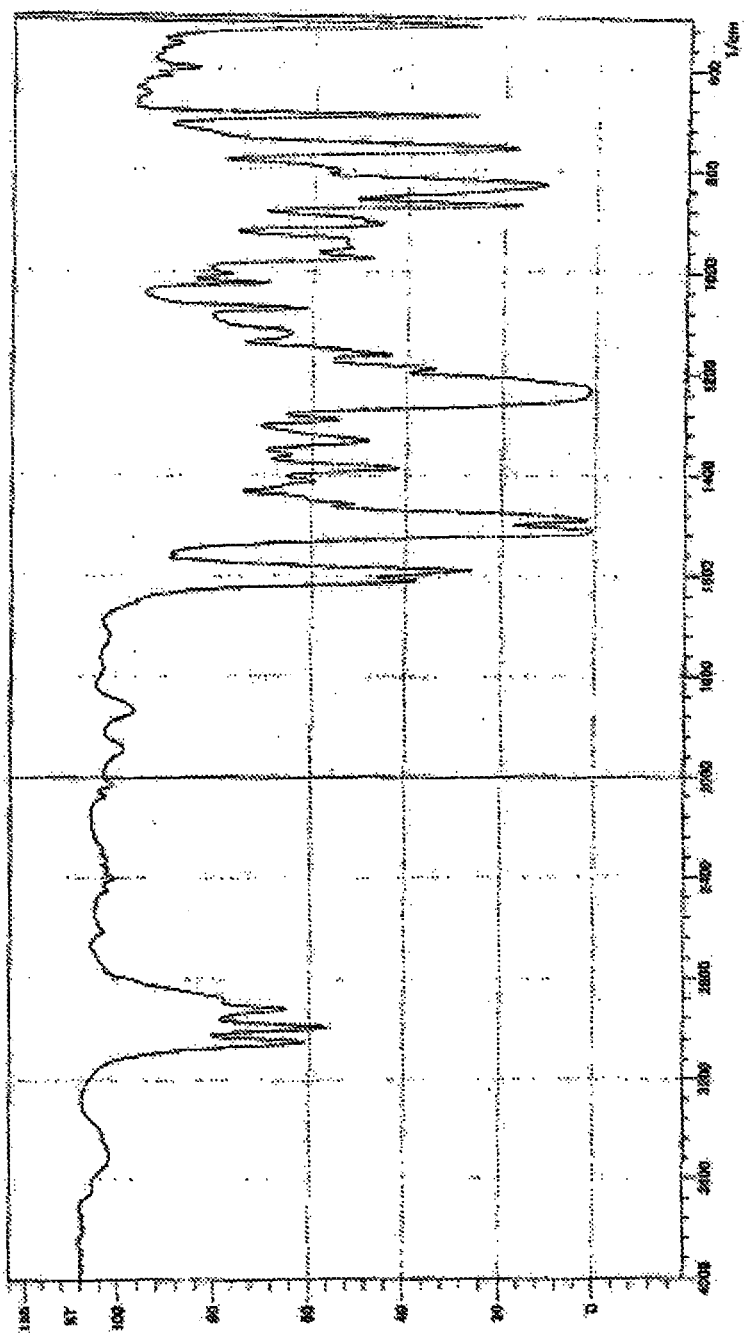
FIG. 3 is an IR chart of the 4-phenoxy-N,N-diglycidylaniline obtained in Example 2.

¹H-NMR charts of the 4-phenoxy-N,N-diglycidylaniline obtained in Example 2 are shown in FIGS. 1 and 2 and an IR chart of the 4-phenoxy-N,N-diglycidylaniline obtained in Example 2 is shown in FIG. 3.

The measurement result of ¹H-NMR (CDCl$_3$, 400 MHz) is summarized as follows:

δ 2.59 (dd, 2H), 2.80 (dd, 2H), 3.15-3.21 (m, 2H), 3.41 (dd, 2H), 3.73 (dd, 2H), 6.81 (d, 2H), 6.93-7.03 (m, 5H), and 7.25-7.30 (m, 2H).

Example 3

Operations were carried out in the same manner as Example 1 except for using no ethanol and adding 203.7 g (1.0 mol) of a powder of 4-phenoxyaniline, yielding 304.7 g (purity: 56.4% (GC area %)) of a brown viscous liquid containing 4-phenoxy-N,N-diglycidylaniline as a main component. The yield of 4-phenoxy-N,N-diglycidylaniline calculated as a pure compound (on the basis of 4-phenoxyaniline) was 52.5%.

Comparative Example 1

Operations were carried out in the same manner as Example 1 except for changing 1018.5 g of ethanol to 1018.5 g of toluene. No addition reaction occurred, so that a desired intermediate, 4-phenoxy-N,N-bis(2-hydroxy-3-chloropropyl)aniline, was not obtained.

Example 4

To a four-necked flask equipped with a thermometer, a cooling tube, and a stirrer were charged with 610.6 g (6.6 mol) of epichlorohydrin and 509.3 g of 2-propanol, and then the inside of the four-necked flask was purged with nitrogen. The temperature was raised to 60° C. and 203.7 g (1.1 mol) of a powder of 4-phenoxyaniline was added over three hours. Moreover, the temperature was raised to 80° C. and the reaction was continued at 80° C. for 18 hours under stirring to produce 4-phenoxy-N,N-bis(2-hydroxy-3-chloropropyl)aniline.

Subsequently, 2-propanol and residual epichlorohydrin were removed by distillation under reduced pressure. To the concentrate were added 407.4 g of toluene and 11.2 g (0.033 mol) of tetrabutyl ammonium hydrogensulfurate. Subsequently, 275 g (3.3 mol) of a 48% aqueous sodium hydroxide solution was dropped at 30° C. over one hour and moreover a cyclization reaction was carried out under stirring at 30° C. for three hours.

After confirming that the cyclization reaction had finished by liquid chromatography, washing with 305.6 g of water was performed. Moreover, 203.7 g of water and 61.1 g of 2-propanol were added to the organic layer, followed by washing. The removal of toluene and epichlorohydrin from the organic layer under reduced pressure provided 317.3 g (purity: 98.0% (GC area %)) of a brown viscous liquid containing 4-phenoxy-N,N-diglycidylaniline as a main component. The yield of 4-phenoxy-N,N-diglycidylaniline calculated by using a purity (on the basis of 4-phenoxyaniline) was 95.1%.

Example 5

Operations were carried out in the same manner as Example 4 except for using no 2-propanol in Example 4. Thus, 312.8 g (purity: 96.6% (GC area %)) of a brown viscous liquid containing 4-phenoxy-N,N-diglycidylaniline as a main component was obtained. The yield of 4-phenoxy-N,N-diglycidylaniline calculated by using a purity (on the basis of 4-phenoxyaniline) was 92.4%.

Example 6

Operations were carried out in the same manner as Example 4 except for changing 11.2 g (0.033 mol) of tetrabutylammonium hydrogensulfate to 12.3 g (0.033 mol) of ethyltriphenylphosphonium bromide in Example 4. Thus, 315.0 g (purity: 96.7% (GC area %)) of a brown viscous liquid containing 4-phenoxy-N,N-diglycidylaniline as a main component was obtained. The yield of 4-phenoxy-N,N-diglycidylaniline calculated by using a purity (on the basis of 4-phenoxyaniline) was 93.1%.

Example 7

Operations were carried out in the same manner as Example 4 except for adding no tetrabutylammonium hydrogensulfate in Example 4. Thus, 294.4 g (purity: 45.1% (GC area %)) of a brown viscous liquid containing 4-phenoxy-N,N-diglycidylaniline as a main component was obtained. The yield of 4-phenoxy-N,N-diglycidylaniline calculated by using a purity (on the basis of 4-phenoxyaniline) was 40.6%.

Example 8

To a four-necked flask equipped with a thermometer, a dropping funnel, a cooling tube, and a stirrer was charged with 509.3 g of 2-propanol, 275 g (3.3 mol) of a 48% aqueous sodium hydroxide solution, and 203.7 g (1.1 mol) of 4-phenoxyaniline, and then the inside of the four-necked flask was purged with nitrogen. The temperature was raised to 80° C. and 610.6 g (6.6 mol) of epichlorohydrin was added over one hour. Moreover, a reaction was carried out under stirring at 80° C. for 18 hours.

After the completion of the reaction, 2-propanol and residual epichlorohydrin were removed by distillation under reduced pressure. To the concentrate was added 407.4 g of toluene. Then washing with 305.6 g of water was performed, and moreover, 203.7 g of water and 61.1 g of 2-propanol were added to the organic layer, followed by washing. The removal of toluene and epichlorohydrin from the organic layer under reduced pressure provided 289.6 g (purity: 84.2% (GC area %)) of a brown viscous liquid containing 4-phenoxy-N,N-diglycidylaniline as a main component. The yield of 4-phenoxy-N,N-diglycidylaniline calculated by using a purity (on the basis of 4-phenoxyaniline) was 74.6%.

Example 9

Operations were carried out in the same manner as Example 4 except for changing 203.7 g (1.1 mol) of the powder of 4-phenoxyaniline to 219.2 g (1.1 mol) of 4-(4-methylphenoxy)aniline in Example 4. Thus, 339.1 g (purity: 97.5% (GC area %)) of a brown viscous liquid containing 4-(4-methylphenoxy)-N,N-diglycidylaniline as a main component was obtained. The yield of 4-(4-methylphenoxy)-N,N-diglycidylaniline calculated by using a purity (on the basis of 4-(4-methylphenoxy)aniline) was 96.5%.

The measurement result of $^1$H-NMR (CDCl$_3$, 400 MHz) is summarized as follows:

δ 2.30 (s, 3H), 2.59 (dd, 2H), 2.80 (dd, 2H), 3.17-3.19 (m, 2H), 3.41 (dd, 2H), 3.72 (dd, 2H), 6.78-6.94 (m, 6H), 7.08 (d, 2H).

Figure 4:
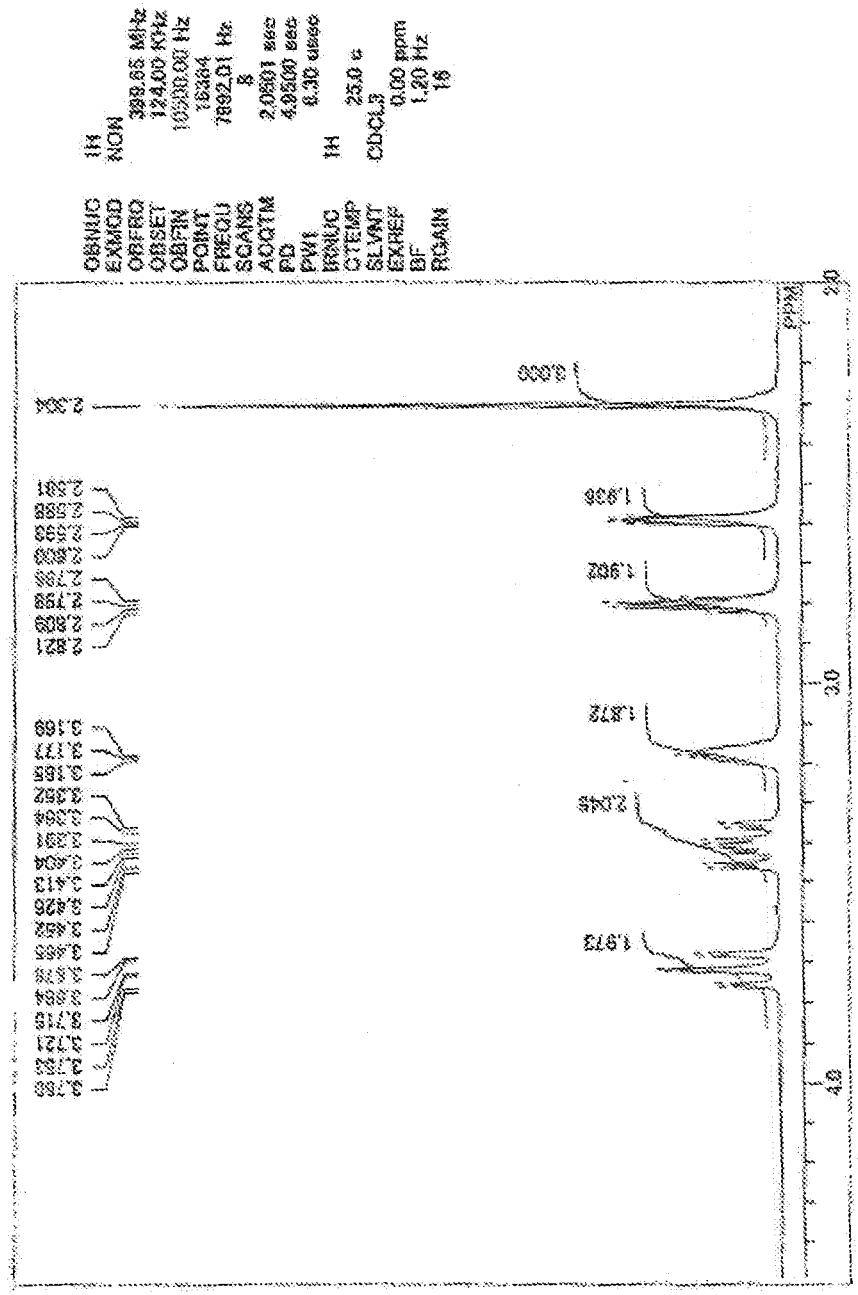
FIG. 4 is a partial enlarged diagram of the $^1$H-NMR chart of the 4-(4-methylphenoxy)-N,N-diglycidylaniline obtained in Example 9.
Figure 5:
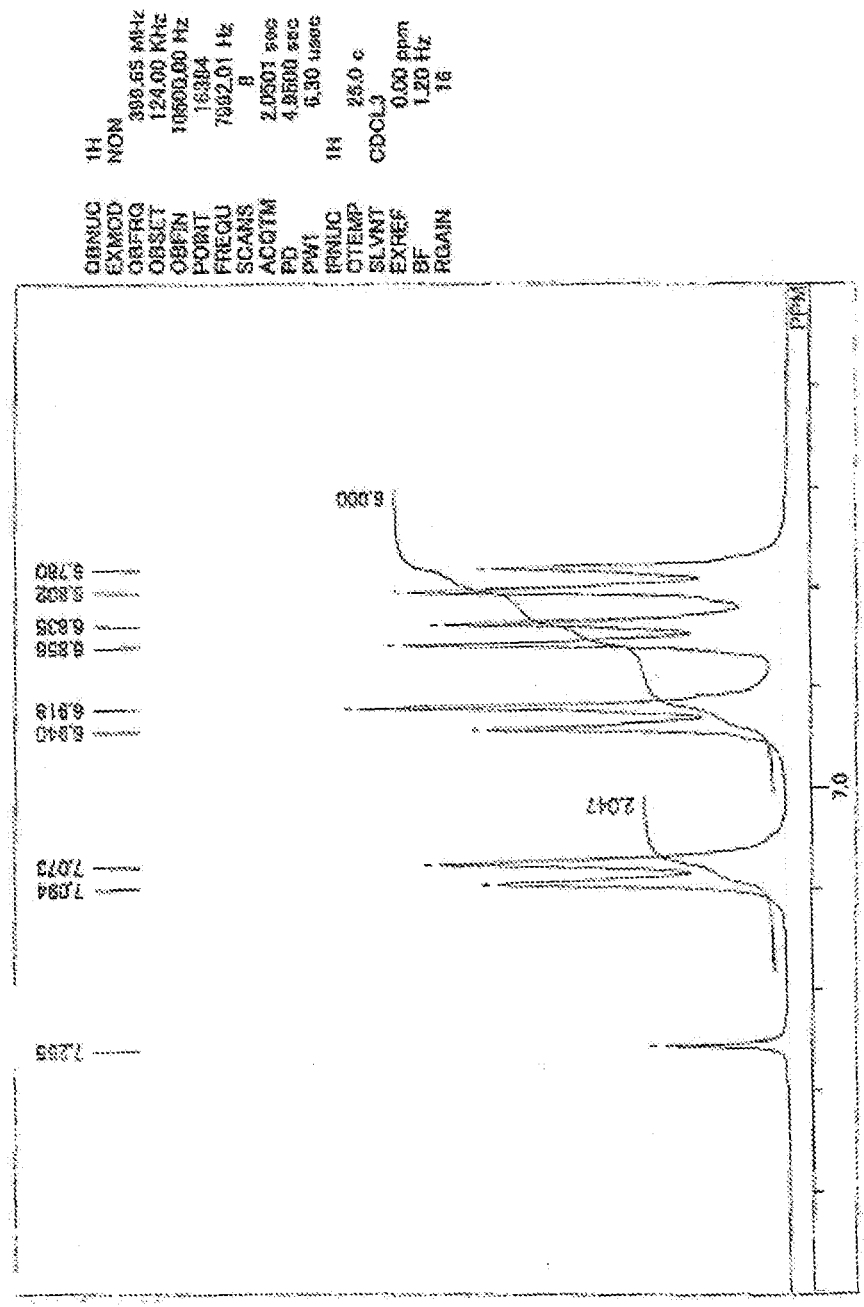
FIG. 5 is a partial enlarged diagram of the $^1$H-NMR chart of the 4-(4-methylphenoxy)-N,N-diglycidylaniline obtained in Example 9.
Figure 6:
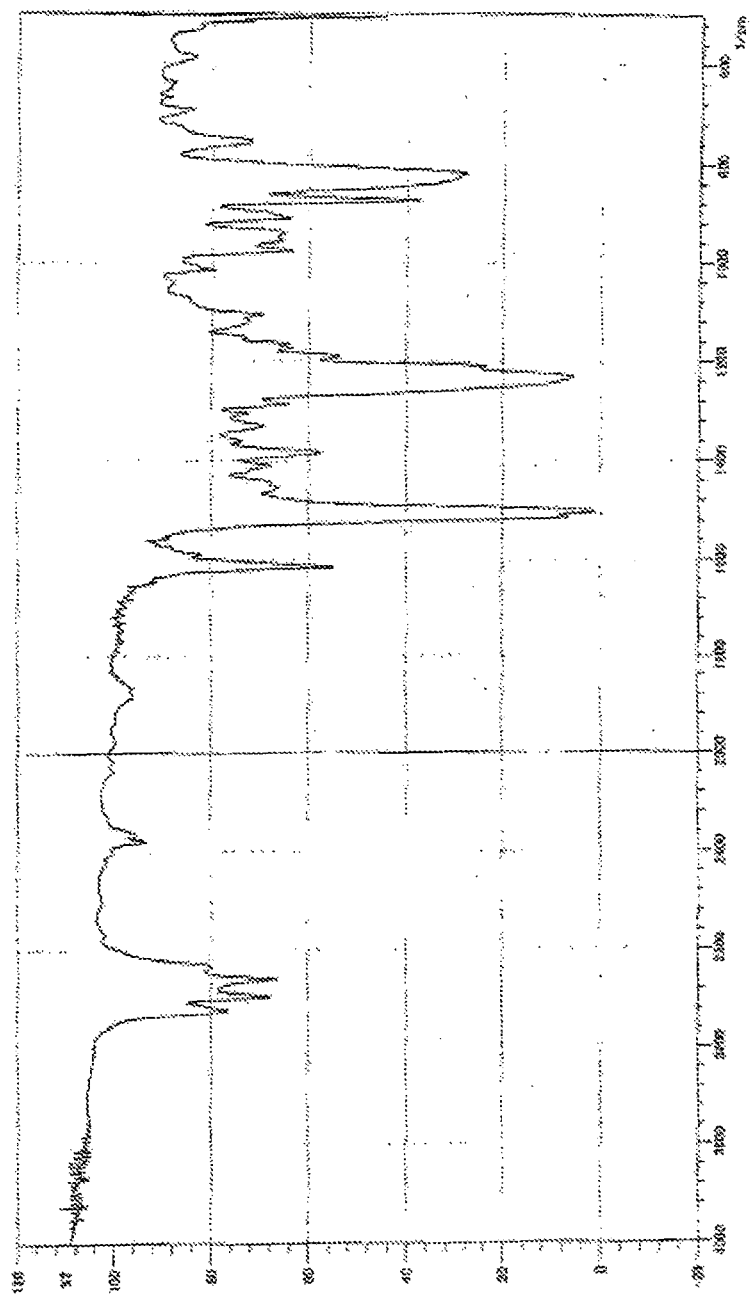
FIG. 6 is an IR chart of the 4-(4-methylphenoxy)-N,N-diglycidylaniline obtained in Example 9.

$^1$H-NMR charts of the 4-(4-methylphenoxy)-N,N-diglycidylaniline obtained in Example 9 are shown in FIGS. 4 and 5 and an IR chart of the 4-(4-methylphenoxy)-N,N-diglycidylaniline obtained in Example 9 is shown in FIG. 6.

Example 10

Operations were carried out in the same manner as Example 4 except for changing 203.7 g (1.1 mol) of the powder of 4-phenoxyaniline to 253.2 g (1.1 mol) of 4-(4-nitrophenoxy)aniline and the reaction time of the addition reaction to 33 hours in Example 4. Thus, 357.8 g (purity: 92.5% (LC area %)) of a brown viscous liquid containing 4-(4-nitrophenoxy)-N,N-diglycidylaniline as a main component was obtained. The yield of 4-(4-nitrophenoxy)-N,N-diglycidylaniline calculated by using a purity (on the basis of 4-(4-nitrophenoxy)aniline) was 87.9%.

The measurement result of $^1$H-NMR (CDCl$_3$, 400 MHz) is summarized as follows:

δ 2.61 (dd, 2H), 2.84 (dd, 2H), 3.20-3.22 (m, 2H), 3.44 (dd, 2H), 3.80 (dd, 2H), 6.85-6.99 (m, 6H), 8.17 (d, 2H).

Figure 7:
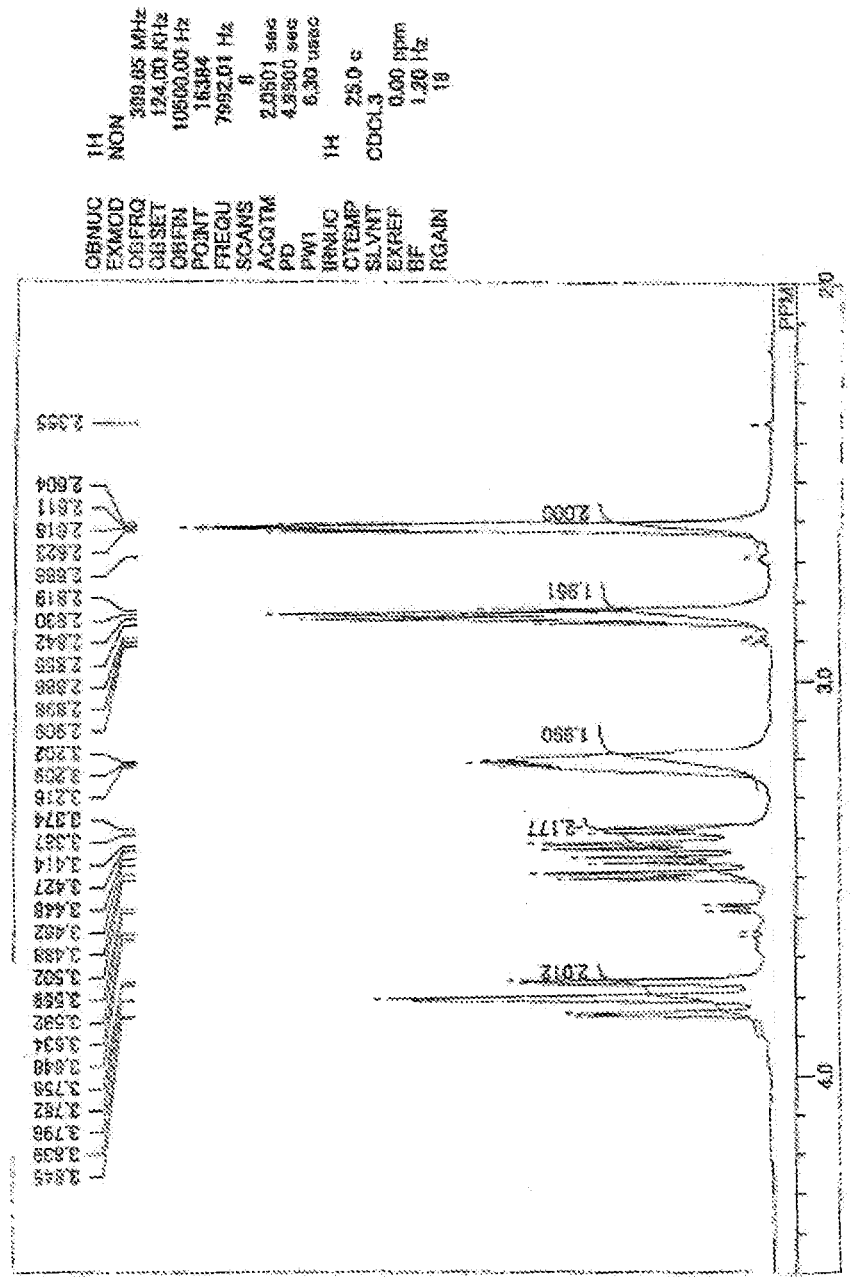
FIG. 7 is a partial enlarged diagram of the $^1$H-NMR chart of the 4-(4-nitrophenoxy)-N,N-diglycidylaniline obtained in Example 10.
Figure 8:
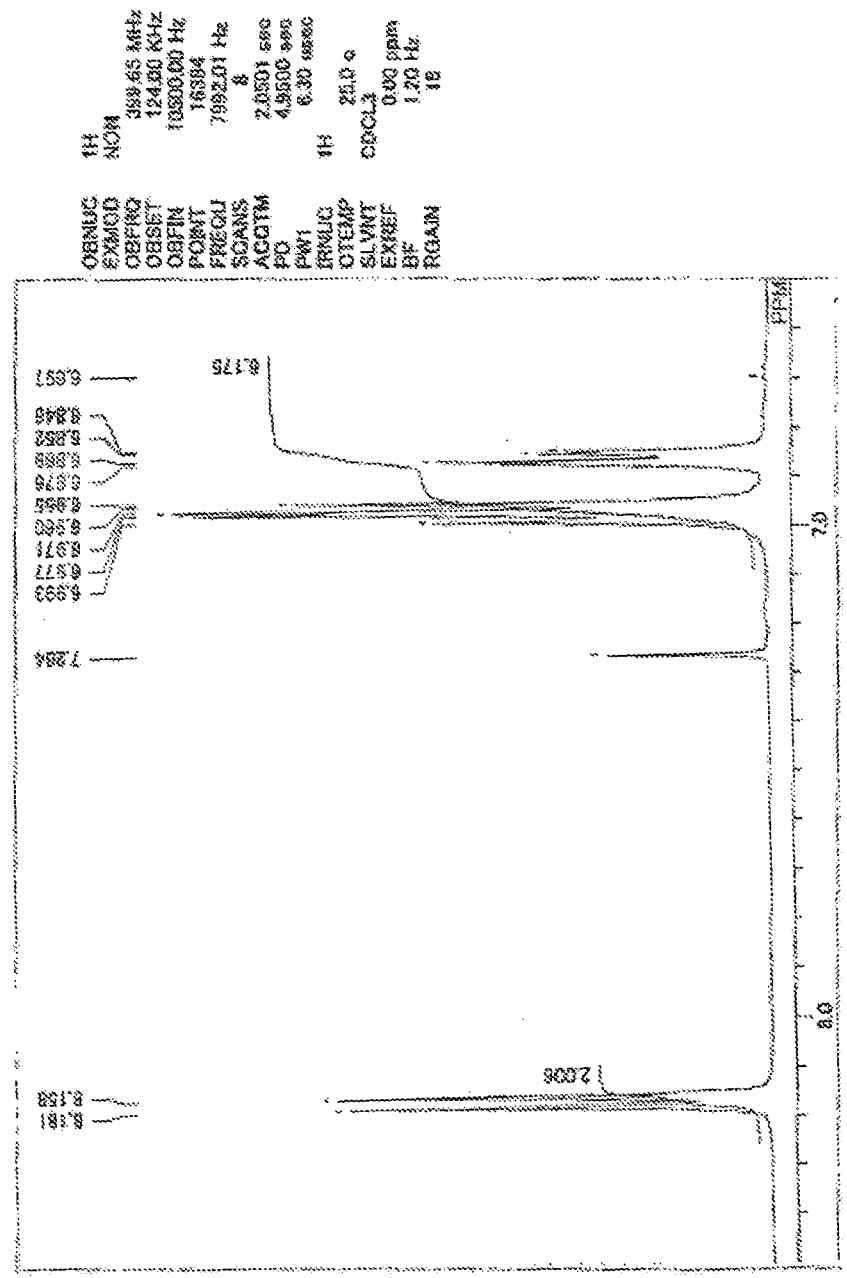
FIG. 8 is a partial enlarged diagram of the $^1$H-NMR chart of the 4-(4-nitrophenoxy)-N,N-diglycidylaniline obtained in Example 10.
Figure 9:
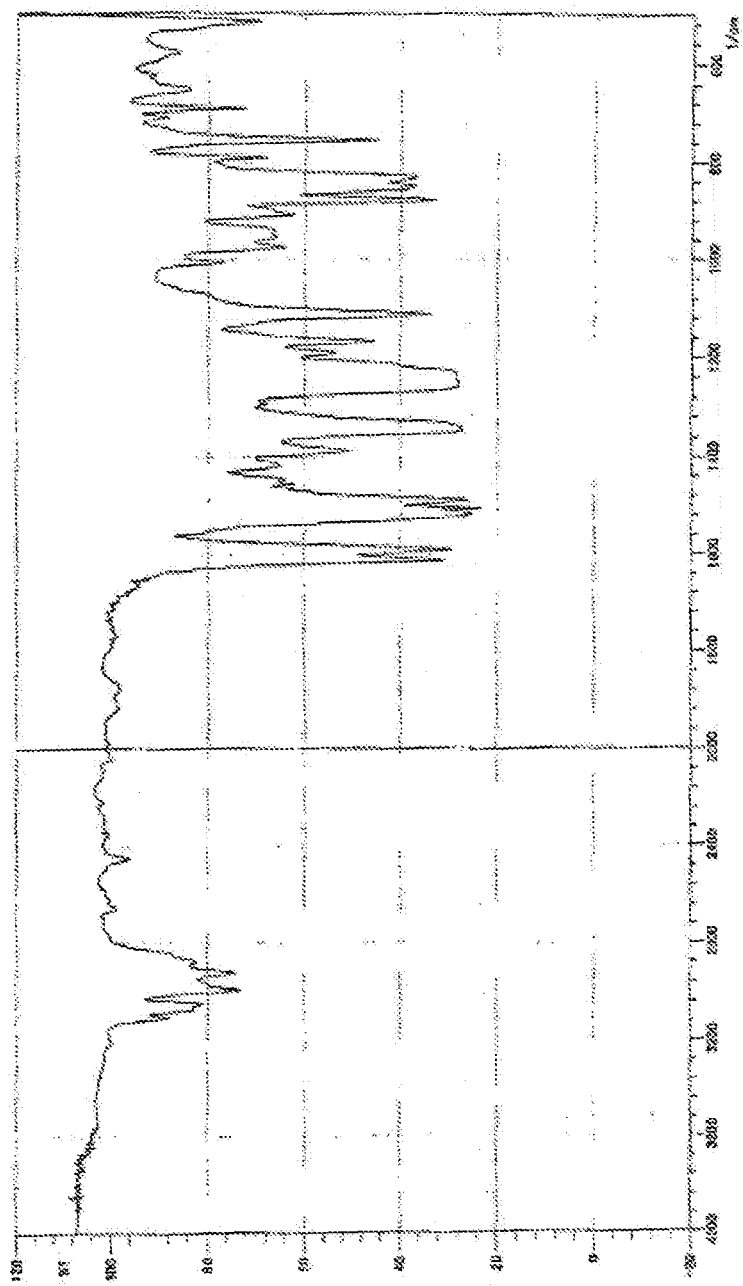
FIG. 9 is an IR chart of the 4-(4-nitrophenoxy)-N,N-diglycidylaniline obtained in Example 10.

$^1$H-NMR charts of the 4-(4-nitrophenoxy)-N,N-diglycidylaniline obtained in Example 10 are shown in FIGS. 7 and 8 and an IR chart of the 4-(4-nitrophenoxy)-N,N-diglycidylaniline obtained in Example 10 is shown in FIG. 9.

Example 11

Operations were carried out in the same manner as Example 4 except for changing 203.7 g (1.1 mol) of the powder of 4-phenoxyaniline to 203.7 g (1.1 mol) of 2-phenoxyaniline and the reaction time of the addition reaction to 47 hours in Example 4. Thus, 320.2 g (purity: 94.5% (GC area %)) of a brown viscous liquid containing 2-phenoxy-N,N-diglycidylaniline as a main component was obtained. The yield of 2-phenoxy-N,N-diglycidylaniline calculated by using a purity (on the basis of 2-phenoxyaniline) was 92.5%.

The measurement result of $^1$H-NMR (CDCl$_3$, 400 MHz) is summarized as follows:

δ 2.46 (dd, 2H), 2.64 (dd, 2H), 2.96-3.03 (m, 2H), 3.23 (dd, 2H), 3.52 (dd, 2H), 6.90-7.13 (m, 6H), 7.20-7.30 (m, 3H).

Figure 10:
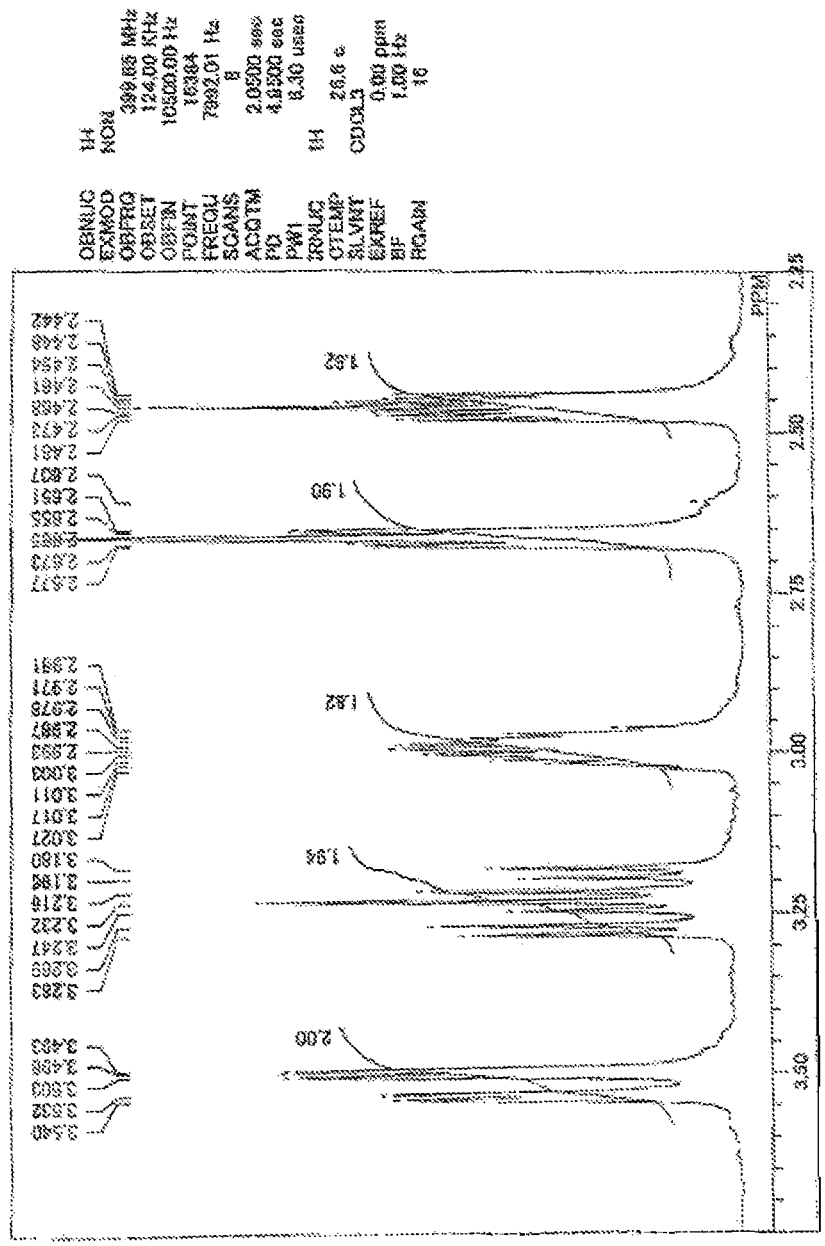
FIG. 10 is a partial enlarged diagram of the $^1$H-NMR chart of the 2-phenoxy-N,N-diglycidylaniline obtained in Example 11.
Figure 11:
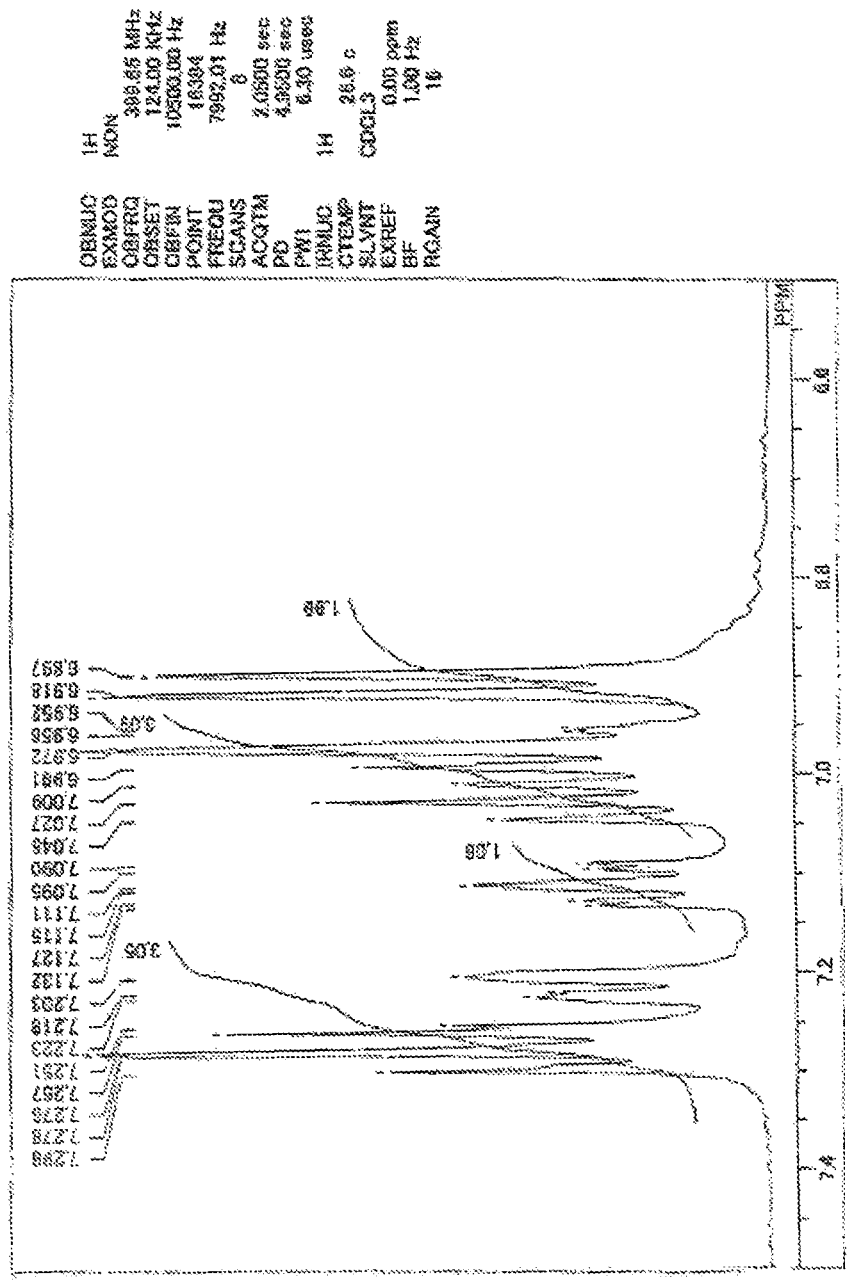
FIG. 11 is a partial enlarged diagram of the $^1$H-NMR chart of the 2-phenoxy-N,N-diglycidylaniline obtained in Example 11.
Figure 12:
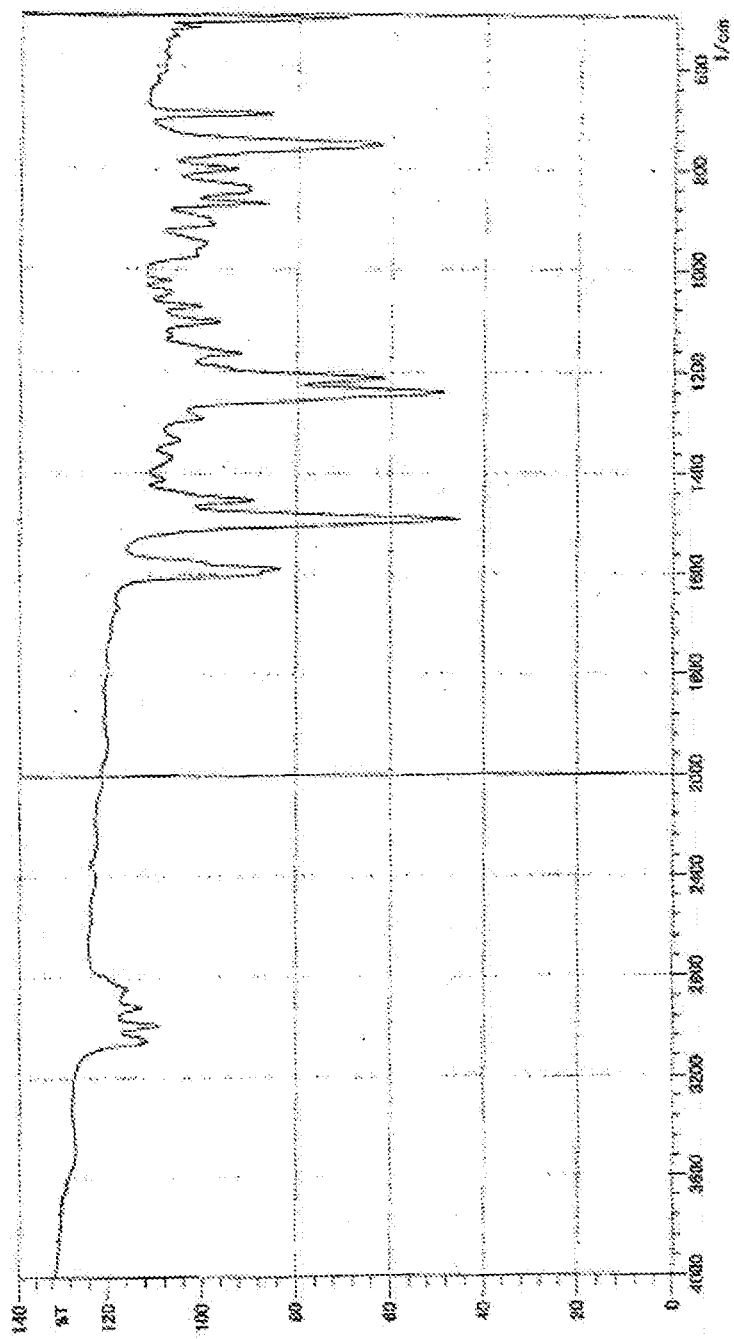
FIG. 12 is an IR chart of the 2-phenoxy-N,N-diglycidylaniline obtained in Example 11.

$^1$H-NMR charts of the 2-phenoxy-N,N-diglycidylaniline obtained in Example 11 are shown in FIGS. 10 and 11 and an IR chart of the 2-phenoxy-N,N-diglycidylaniline obtained in Example 11 is shown in FIG. 12.

Example 12

Operations were carried out in the same manner as Example 11 except for changing the amount of epichlorohydrin added to 1221.2 g (13.2 mol), changing 509.3 g of 2-propanol to 509.3 g of propylene glycol monomethyl ether, and changing the reaction time of the addition reaction to 21 hours and the temperature of the addition reaction to 110° C. in Example 11. Thus, 319.3 g (purity: 97.1% (GC area %)) of a brown viscous liquid containing 2-phenoxy-N,N-diglycidylaniline as a main component was obtained. The yield of 2-phenoxy-N,N-diglycidylaniline calculated by using a purity (on the basis of 2-phenoxyaniline) was 94.8%.

Example 13

Operations were carried out in the same manner as Example 4 except for changing 203.7 g (1.1 mol) of the powder of 4-phenoxyaniline to 219.2 g (1.1 mol) of 2-(2-methylphenoxy)aniline and the ripening time of the addition reaction to 32 hours in Example 4. Thus, 336.5 g (purity: 96.2% (GC area %)) of a brown viscous liquid containing 2-(2-methylphenoxy)-N,N-diglycidylaniline as a main component was obtained. The yield of 2-(2-methylphenoxy)-N,N-diglycidylaniline calculated by using a purity (on the basis of 2-(2-methylphenoxy)aniline) was 94.5%.

The measurement result of $^1$H-NMR (CDCl$_3$, 400 MHz) is summarized as follows:

δ 2.31 (s, 3H), 2.50 (dd, 2H), 2.69 (dd, 2H), 3.06-3.07 (m, 2H), 3.29 (dd, 2H), 3.56 (dd, 2H), 6.74 (dd, 2H), 6.93-7.12 (m, 4H), 7.21-7.25 (m, 2H).

Figure 13:
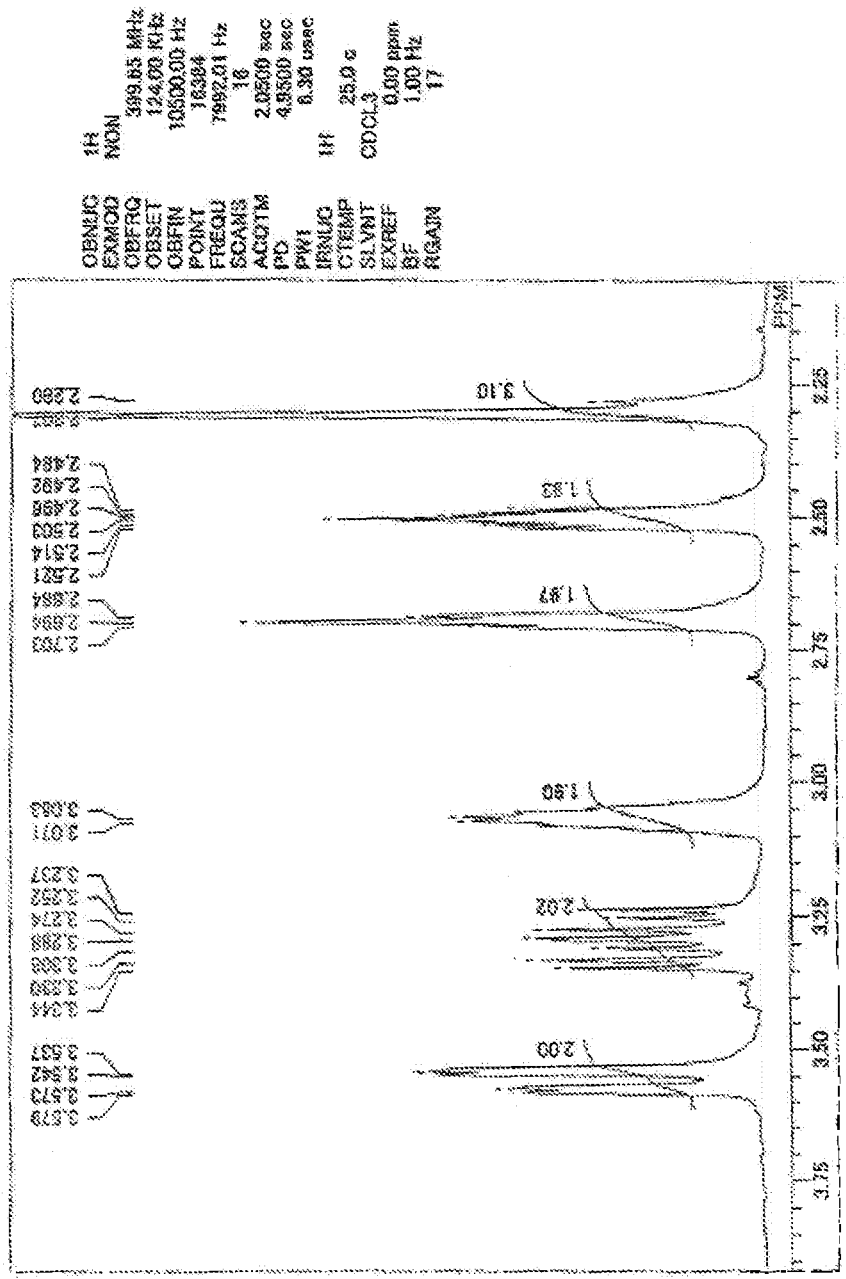
FIG. 13 is a partial enlarged diagram of the $^1$H-NMR chart of the 2-(2-methylphenoxy)-N,N-diglycidylaniline obtained in Example 13.
Figure 14:
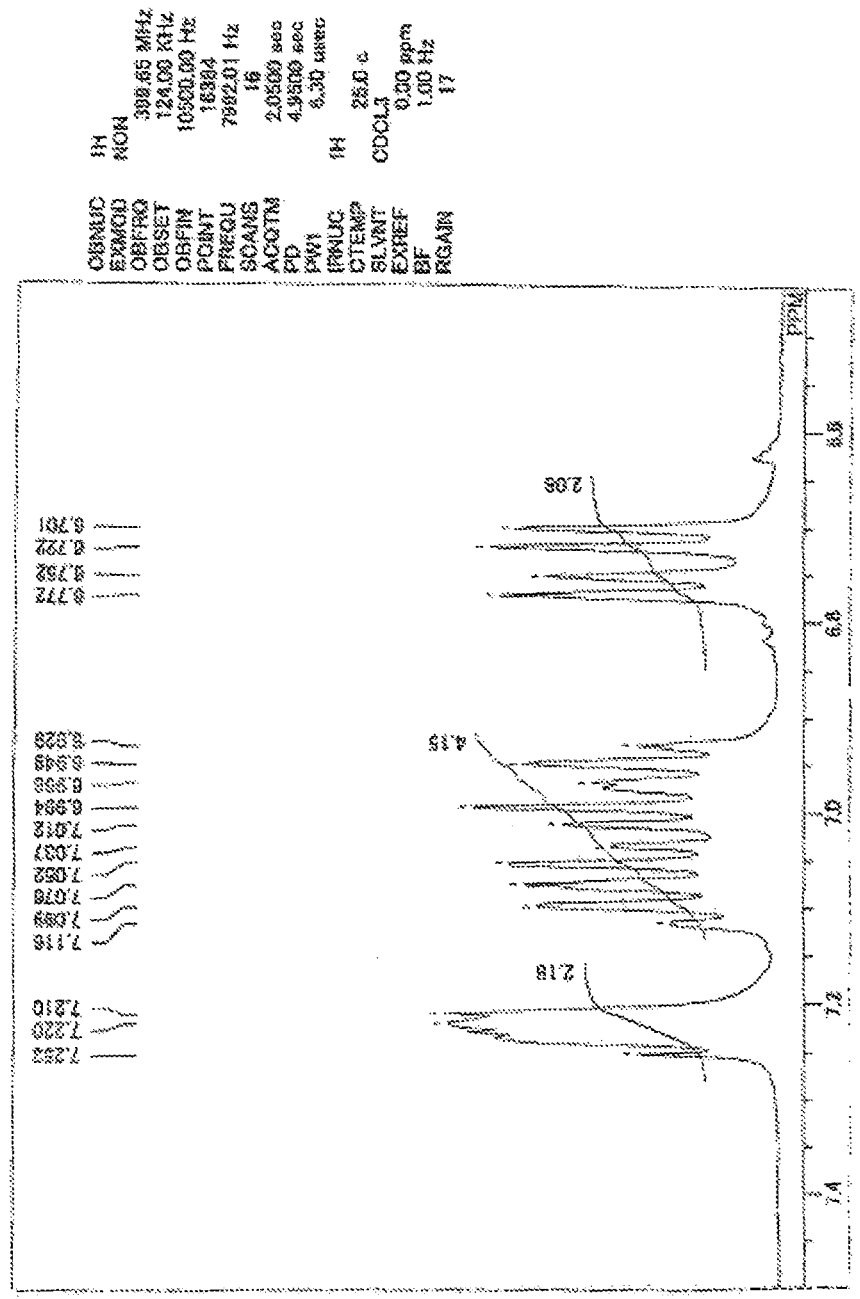
FIG. 14 is a partial enlarged diagram of the $^1$H-NMR chart of the 2-(2-methylphenoxy)-N,N-diglycidylaniline obtained in Example 13.
Figure 15:
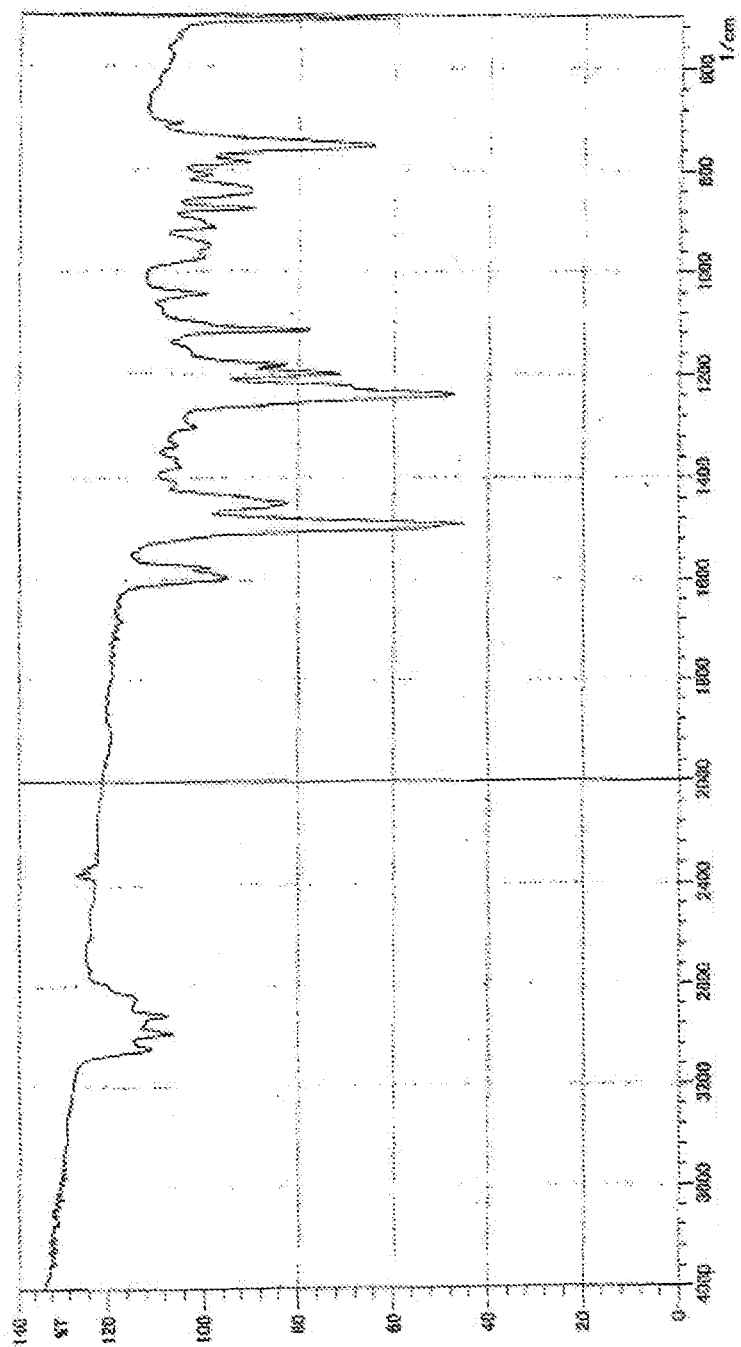
FIG. 15 is an IR chart of the 2-(2-methylphenoxy)-N,N-diglycidylaniline obtained in Example 13.

$^1$H-NMR charts of the 2-(2-methylphenoxy)-N,N-diglycidylaniline obtained in Example 13 are shown in FIGS. 13 and 14 and an IR chart of the 2-(2-methylphenoxy)-N,N-diglycidylaniline obtained in Example 13 is shown in FIG. 15.

Example 14

Operations were carried out in the same manner as Example 4 except for changing 203.7 g (1.1 mol) of the powder of 4-phenoxyaniline to 203.7 g (1.1 mol) of 3-phenoxyaniline and the reaction time of the addition reaction to 30 hours in Example 4. Thus, 319.8 g (purity: 97.5% (GC area %)) of a brown viscous liquid containing 3-phenoxy-N,N-diglycidylaniline as a main component was obtained. The yield of 3-phenoxy-N,N-diglycidylaniline calculated by using a purity (on the basis of 3-phenoxyaniline) was 95.3%.

The measurement result of $^1$H-NMR (CDCl$_3$, 400 MHz) is summarized as follows:

δ 2.55 (dd, 2H), 2.78 (dd, 2H), 3.13-3.18 (m, 2H), 3.43 (dd, 2H), 3.72 (dd, 2H), 6.35 (dd, 1H), 6.47 (s, 1H), 6.54 (dd, 1H), 7.01-7.03 (m, 2H), 7.09 (dd, 1H), 7.17 (t, 1H), 7.31-7.34 (m, 2H).

Figure 16:
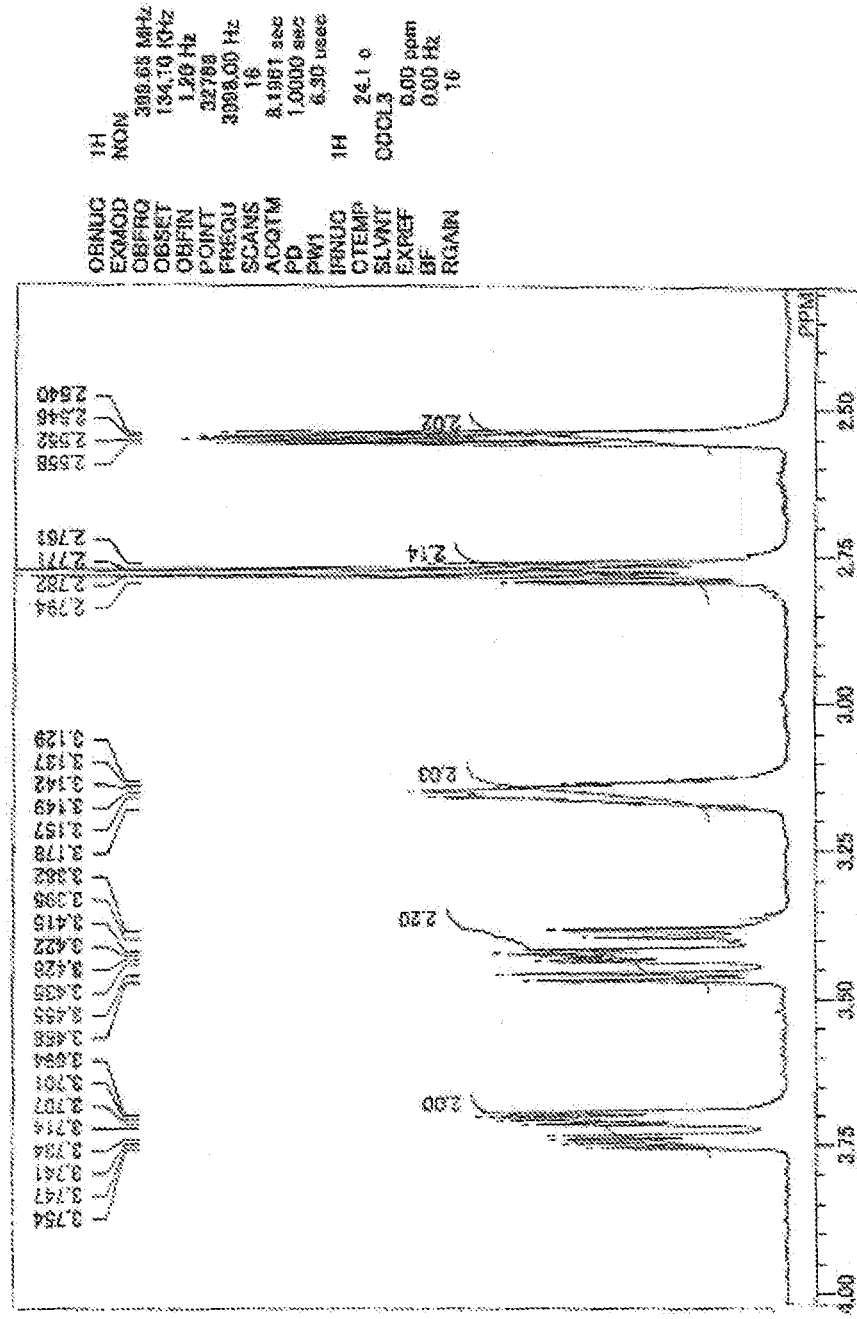
FIG. 16 is a partial enlarged diagram of the $^1$H-NMR chart of the 3-phenoxy-N,N-diglycidylaniline obtained in Example 14.
Figure 17:
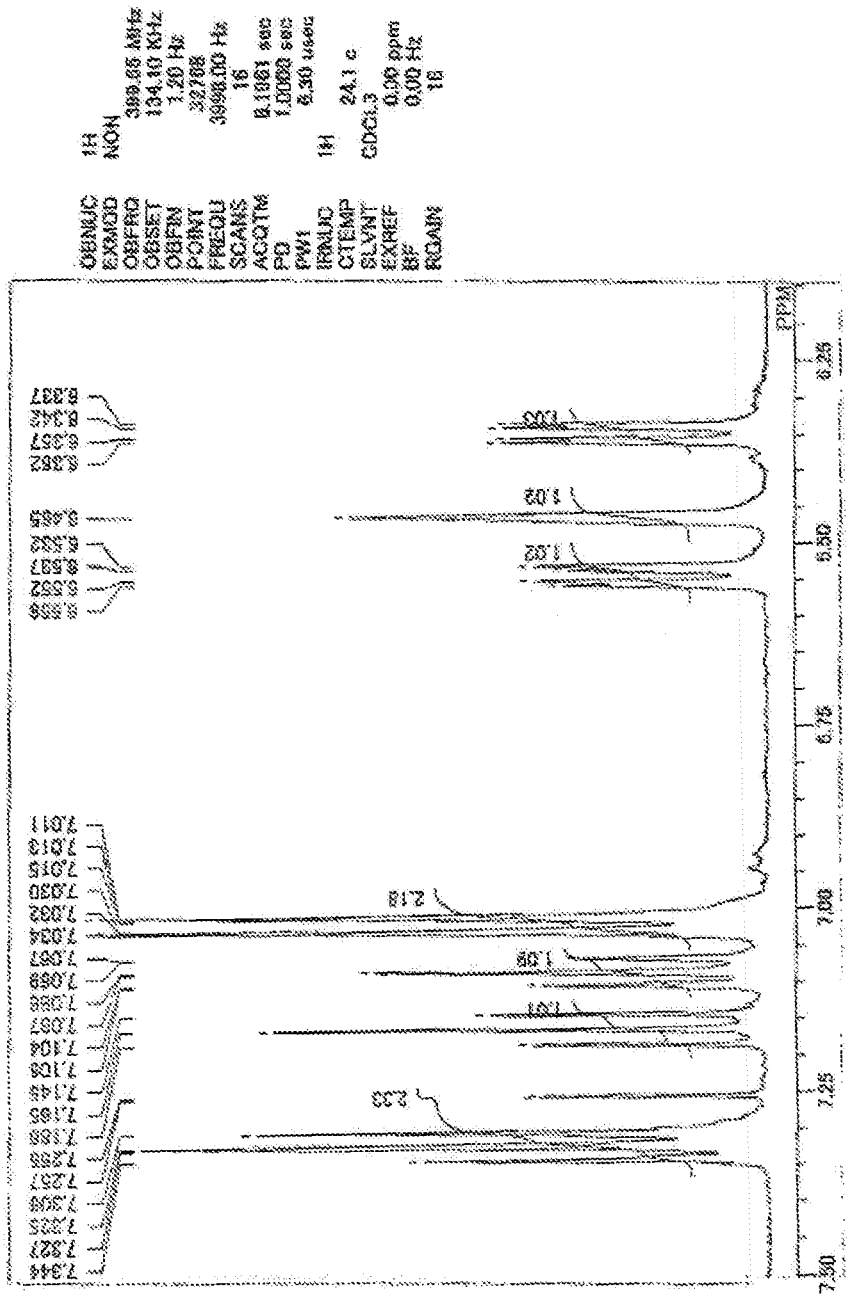
FIG. 17 is a partial enlarged diagram of the $^1$H-NMR chart of the 3-phenoxy-N,N-diglycidylaniline obtained in Example 14.
Figure 18:
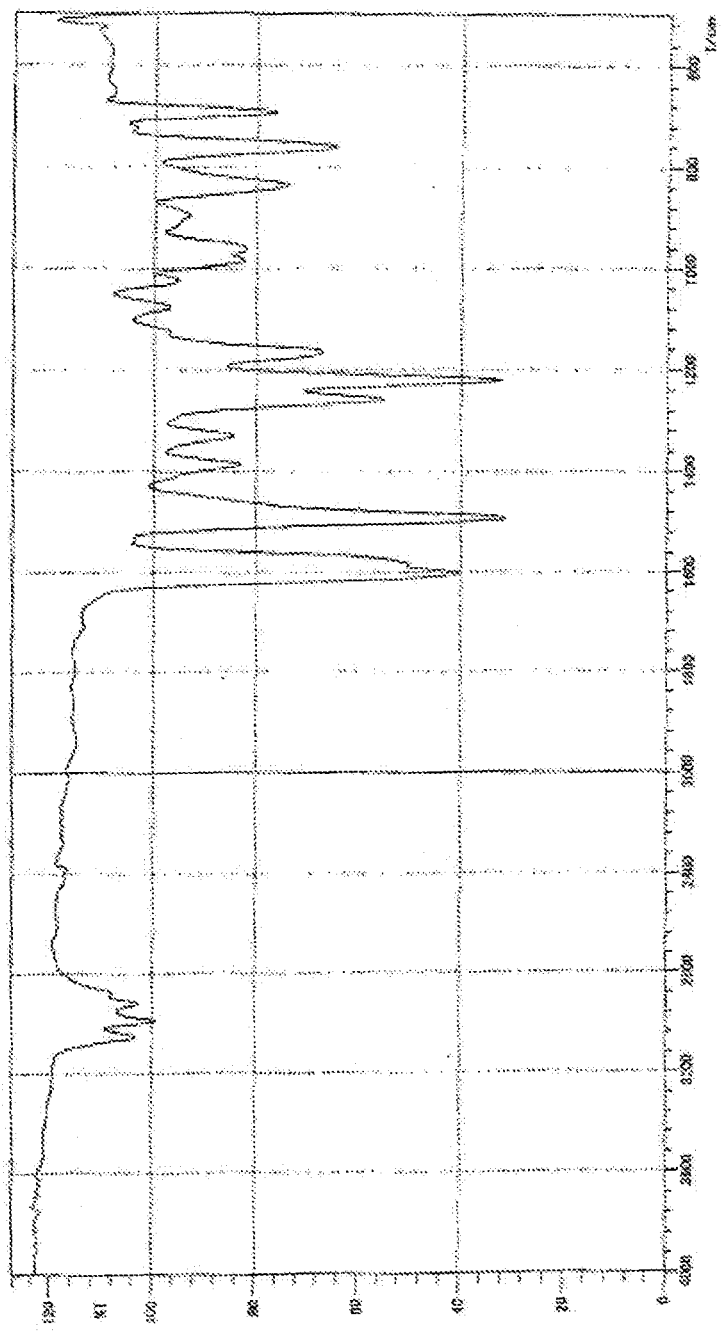
FIG. 18 is an IR chart of the 3-phenoxy-N,N-diglycidyla-niline obtained in Example 14.

$^1$H-NMR charts of the 3-phenoxy-N,N-diglycidylaniline obtained in Example 14 are shown in FIGS. 16 and 17 and an IR chart of the 3-phenoxy-N,N-diglycidylaniline obtained in Example 14 is shown in FIG. 18.

Referential Example 1

A liquid composition was prepared by uniformly mixing 41 parts by weight of metaxylenediamine (MXDA, produced by Mitsubishi Gas Chemical Co., Ltd.) as a curing agent to a mixture of 60 parts by weight of the 4-phenoxy-N,N-diglycidylaniline obtained in Example 1 and 40 parts by weight of bisphenol A-modified epoxy resin (jER828, produced by Japan Epoxy Resins Co., Ltd.). This liquid composition was poured into a mold and then was heated at 140° C. for two hours to cure. A specimen was produced from the cured product. The elastic modulus of the cured product was measured with a dynamic viscoelasticity analyzer (DMA) (Rheogel-E4000, manufactured by UBM) at temperature rising rate of 2° C./min.

The elastic modulus at 30° C. of a cured product was 2.8 GPa, and the elastic modulus at 120° C. was 2.9 MPa.

INDUSTRIAL APPLICATION

A high-performance cured epoxy resin that is high in strength, elastic modulus, adhesiveness, toughness, heat resistance, weather resistance, solvent resistance, impact resistance, and so on can be obtained by curing the epoxy compound with an amine. The epoxy compound is useful in a wide variety of fields for industrial applications, such as fine chemicals, medical and agrochemical intermediates, resin raw materials, and further electronic information materials and optical materials.

When the epoxy compound and an ordinary epoxy resin are mixed and cured with an amine, a cured product that can be used for an adhesive or a paint, for example, can be obtained.

The method for producing an epoxy compound can produce a useful epoxy compound.

The invention claimed is:

1. An epoxy compound represented by the following formula:

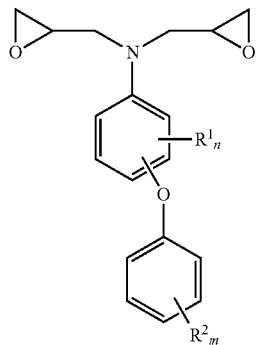

wherein $R^1$ and $R^2$ are members selected from the group consisting of hydrogen, aliphatic hydrocarbon group having 1 to 4 carbon atoms, alicyclic hydrocarbon group having 3 to 6 carbon atoms, aromatic hydrocarbon group having 6 to 10 carbon atoms, halogen atom, ether group, ester group, acyl group and nitro group, n is an integer of 1 to 4, and m is an integer of 1 to 5.

2. The epoxy compound according to claim 1, wherein $R^1$ is hydrogen, an aliphatic hydrocarbon group having 1 to 4 carbon atoms, or an aromatic hydrocarbon group having 6 to 9 carbon atoms.

3. The epoxy compound according to claim 1, wherein $R^2$ is hydrogen, an aliphatic hydrocarbon group having 1 to 4 carbon atoms, an aromatic hydrocarbon group having 6 to 9 carbon atoms, or a nitro group.

4. The epoxy compound according to claim 1, wherein $R^1$ is hydrogen.

5. The epoxy compound according to claim 1, wherein $R^2$ is hydrogen, a methyl group, or a nitro group.

6. An epoxy compound represented by the following formula:

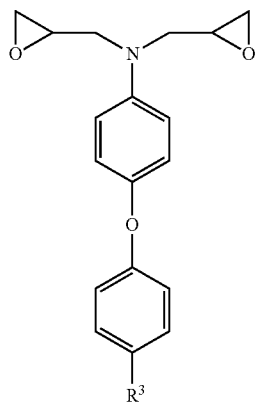

wherein $R^3$ is hydrogen, a methyl group, or a nitro group.

7. An epoxy compound represented by the following formula:

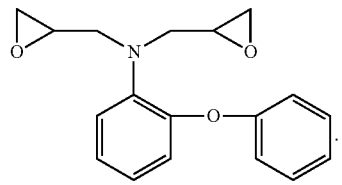 [SMILES: c1ccc(Oc2ccccc2N(CC2CO2)CC2CO2)cc1]

8. An epoxy compound represented by the following formula:

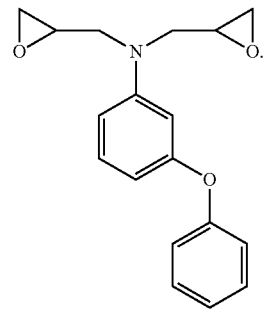 [SMILES: c1ccc(Oc2cccc(N(CC3CO3)CC3CO3)c2)cc1]

9. A method for producing an epoxy compound represented by the following formula:

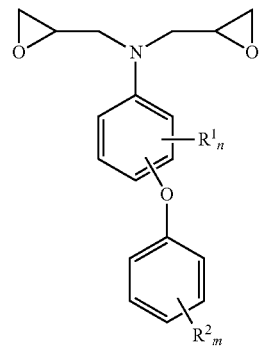

wherein $R^1$ and $R^2$ are members selected from the group consisting of hydrogen, aliphatic hydrocarbon group having 1 to 4 carbon atoms, alicyclic hydrocarbon group having 3 to 6 carbon atoms, aromatic hydrocarbon group having 6 to 10 carbon atoms, halogen atom, ether group, ester group, acyl group and nitro group, a is an integer of 1 to 4, and m is an integer of 1 to 5, comprising:

reacting a phenoxyaniline compound represented by the following formula:

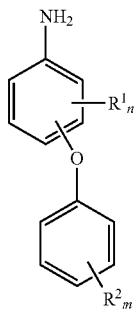

wherein R¹ and R² are members selected from the group consisting of hydrogen, aliphatic hydrocarbon group having 1 to 4 carbon atoms, alicyclic hydrocarbon group having 3 to 6 carbon atoms, aromatic hydrocarbon group having 6 to 10 carbon atoms, halogen atom, ether group, ester group, acyl group and nitro group, n is an integer of 1 to 4, and m is an integer of 1 to 5, and epichlorohydrin.

10. The method according to claim 9, further comprising reacting the phenoxyaniline compound and the epichlorohydrin in a solvent containing an alcohol.

11. The method for producing an epoxy compound according to claim 10, further comprising:

reacting the phenoxyaniline compound and the epichlorohydrin in a solvent containing an alcohol, reacting the formed dichlorohydrin compound represented by the following formula:

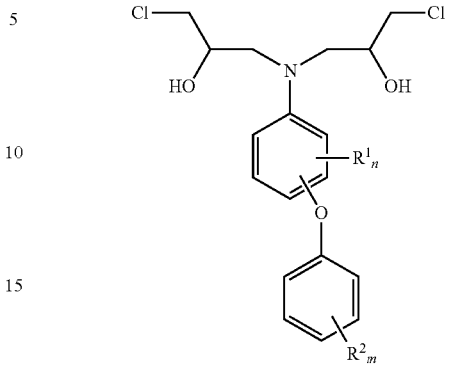

wherein R¹ and R² are members selected from the group consisting of hydrogen, aliphatic hydrocarbon group having 1 to 4 carbon atoms, alicyclic hydrocarbon group having 3 to 6 carbon atoms, aromatic hydrocarbon group having 6 to 10 carbon atoms, halogen atom, ether group, ester group, acyl group and nitro group, n is an integer of 1 to 4, and m is an integer of 1 to 5, and an alkali compound, and producing a diepoxy compound by dehydrochlorination.

12. The method according to claim 11, wherein producing a diepoxy compound from the dichlorohydrin compound by dehydrochlorination includes a quaternary ammonium salt and/or a quaternary phosphonium salt with a diepoxy compound and/or the dichlorohydrin compound.

13. The method according to claim 9, wherein R¹ is hydrogen or an aliphatic hydrocarbon group having 1 to 4 carbon atoms.

14. The method according to claim 9, wherein R² is hydrogen, an aliphatic hydrocarbon group having 1 to 4 carbon atoms, or a nitro group.

15. The method according to claim 9, wherein R¹ is hydrogen.

16. The method according to claim 9, wherein R² is hydrogen, a methyl group, or a nitro group.

* * * * *